(12) United States Patent
Ueda et al.

(10) Patent No.: US 10,281,615 B2
(45) Date of Patent: May 7, 2019

(54) NEAR-INFRARED ABSORBING AGENT AND NEAR-INFRARED ABSORBING COMPOSITION

(71) Applicant: ADEKA CORPORATION, Tokyo (JP)

(72) Inventors: Naoto Ueda, Saitama (JP); Kazukiyo Nomura, Saitama (JP)

(73) Assignee: Adeka Corporation, Tokyo (JP)

( * ) Notice: Subject to any disclaimer, the term of this patent is extended or adjusted under 35 U.S.C. 154(b) by 890 days.

(21) Appl. No.: 14/410,339

(22) PCT Filed: Jun. 4, 2013

(86) PCT No.: PCT/JP2013/065507
§ 371 (c)(1),
(2) Date: Dec. 22, 2014

(87) PCT Pub. No.: WO2014/002705
PCT Pub. Date: Jan. 3, 2014

(65) Prior Publication Data
US 2015/0323702 A1    Nov. 12, 2015

(30) Foreign Application Priority Data

Jun. 28, 2012  (JP) ................. 2012-145193

(51) Int. Cl.
| G02B 1/04 | (2006.01) |
| G02B 5/20 | (2006.01) |
| C07D 471/22 | (2006.01) |
| C07D 487/22 | (2006.01) |
| C08K 5/00 | (2006.01) |

(52) U.S. Cl.
CPC ............. *G02B 1/04* (2013.01); *C07D 471/22* (2013.01); *C07D 487/22* (2013.01); *C08K 5/0091* (2013.01); *G02B 5/208* (2013.01)

(58) Field of Classification Search
USPC ........................................... 524/88; 252/586
See application file for complete search history.

(56) References Cited

U.S. PATENT DOCUMENTS

| 6,468,713 B1 | 10/2002 | Terao et al. | |
| 6,680,350 B1 * | 1/2004 | Dobler | C08K 5/3417 524/88 |
| 2011/0311911 A1 | 12/2011 | Kimura et al. | |

FOREIGN PATENT DOCUMENTS

| CN | 102334017 A | 1/2012 |
| JP | 8-134389 A | 5/1996 |
| JP | 2000-281919 A | 10/2000 |
| JP | 2005-120315 A | 5/2005 |
| JP | 2007-316255 A | 12/2007 |
| JP | 2007316255 | * 12/2007 |
| JP | 2010-197305 A | 9/2010 |
| WO | WO 2008/083918 A1 | 7/2008 |

OTHER PUBLICATIONS

International Search Report, issued in PCT/JP2013/065507, dated Jul. 30, 2013.
Chinese Office Action and Search Report, dated Aug. 13, 2015, for Chinese Application No. 201380034502.X.
Extended European Search Report dated Nov. 5, 2015 for Application No. 13808542.8.

* cited by examiner

*Primary Examiner* — Monique R Peets
(74) *Attorney, Agent, or Firm* — Birch, Stewart, Kolasch & Birch, LLP

(57) ABSTRACT

Provided are: a near-infrared absorbing agent and a near-infrared absorbing composition, which have excellent near-infrared absorbing capacity; and a near-infrared absorbing resin composition in which the physical properties intrinsic to a resin are not impaired. The near-infrared absorbing agent comprises a phthalocyanine compound represented by the following Formula (1):

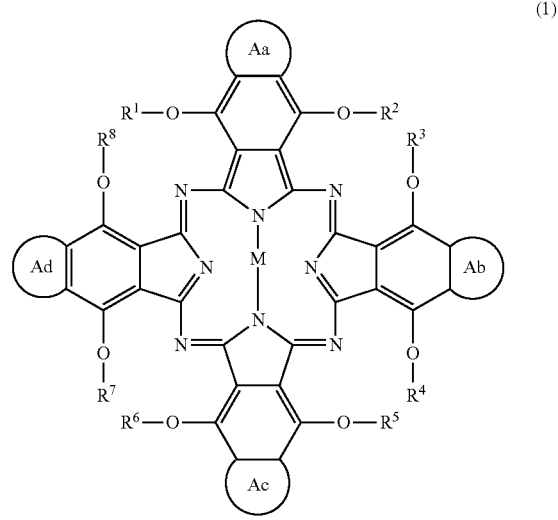

(1)

(wherein, M represents two hydrogen atoms or the like; $R^1$ to $R^8$ may be the same or different from each other and each represent an alkyl group having 1 to 20 carbon atoms which is optionally substituted, or the like; and Aa, Ab, Ac and Ad each independently represent a cyclic structure represented by Formula (2), (3), or (4), with a proviso that at least one, but not all, of Aa, Ab, Ac and Ad is the cyclic structure represented by the Formula (4)).

10 Claims, 3 Drawing Sheets

[Fig. 1]
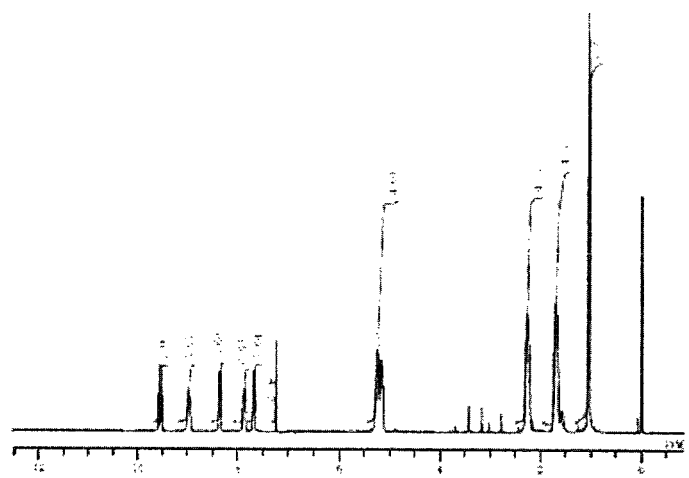
[Fig. 2]
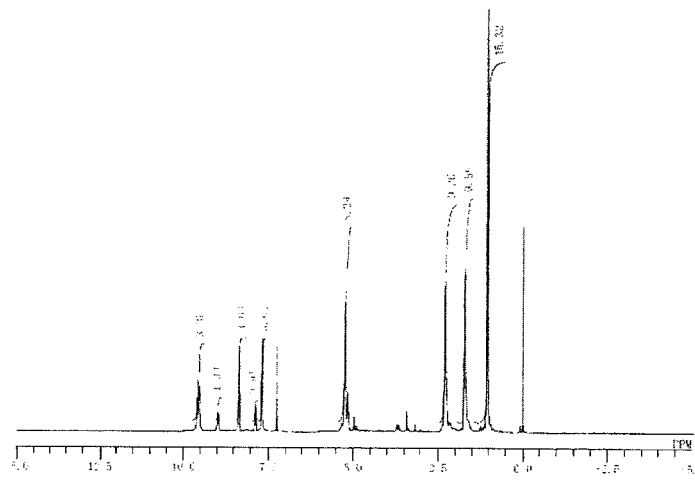

[Fig. 3]
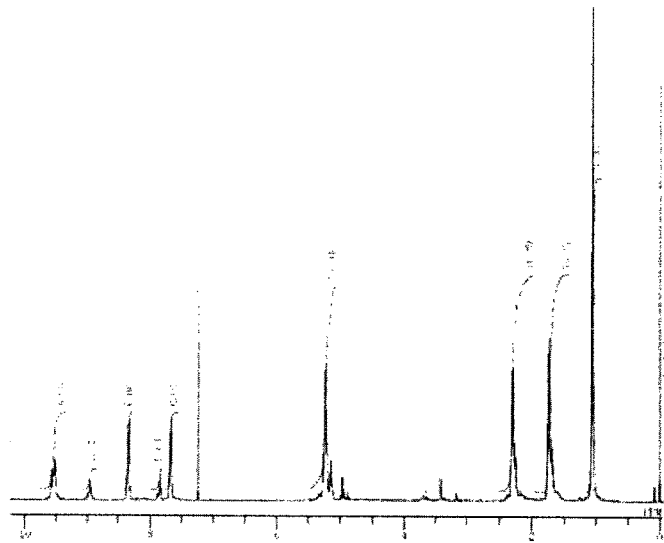
[Fig. 4]
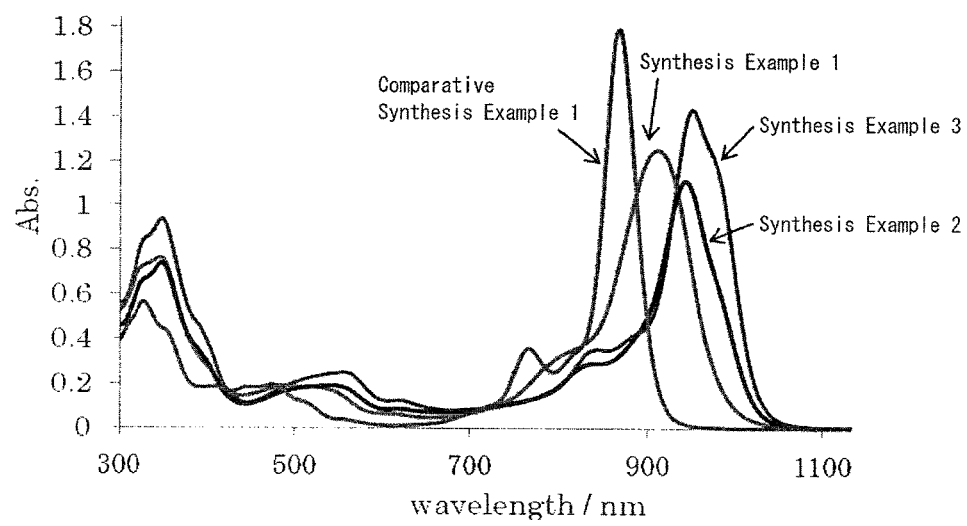

[Fig. 5]
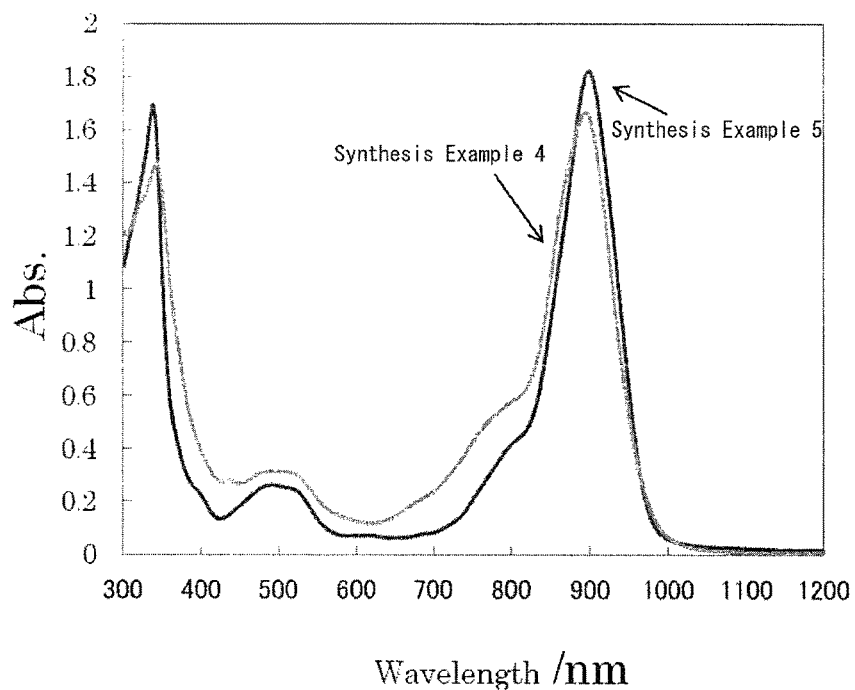
[Fig. 6]
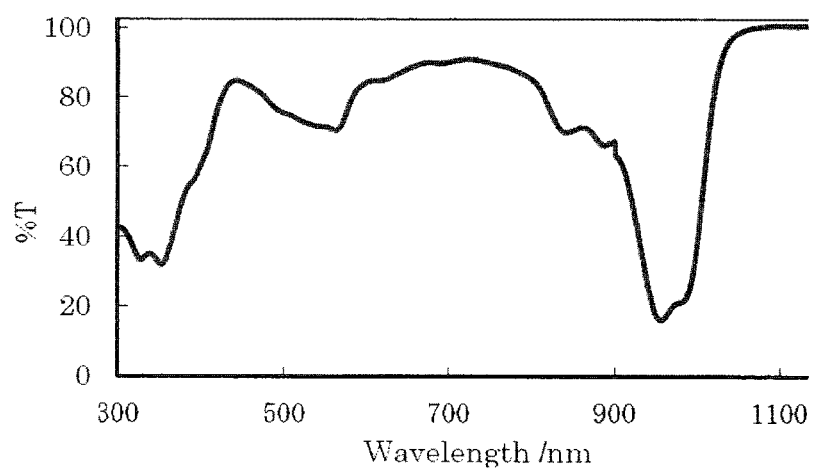

NEAR-INFRARED ABSORBING AGENT AND NEAR-INFRARED ABSORBING COMPOSITION

TECHNICAL FIELD

The present invention relates to a near-infrared absorbing agent, a near-infrared absorbing composition comprising the same, and a near-infrared absorbing resin composition. More particularly, the present invention relates to a near-infrared absorbing agent, a near-infrared absorbing composition and a near-infrared absorbing resin composition, which show absorption in the near-infrared region and are useful for information recording materials utilizing laser light and various other applications where near-infrared absorbing capacity (or heat ray-absorbing capacity) is required.

BACKGROUND ART

In recent years, various applications of near-infrared absorbing materials (heat ray-shielding materials) that absorb near-infrared radiation have been proposed; however, there is a strong demand for a near-infrared absorbing material that exhibits even superior performance.

For example, materials such as methacrylic resins and polycarbonate resins have been used in so-called glazing applications including windows of buildings and vehicles such as automobiles as well as roof windows, doors and roof domes, and there is a demand for a material that is capable of inhibiting an increase in the room temperature while allowing visible light to be sufficiently taken in.

Also, in plant cultivation, greenhouses and vinyl houses are actively used for the purposes of, for example, improving the yields of agricultural crops and shifting the harvest time, and there is a demand for a film that effectively shields heat rays without substantially hindering the transmission of visible light required for plant growth.

Further, near-infrared radiation is often used for driving and stopping electric appliances that perform recording and playing of an information recording medium such as magnetic tape and, in such electric appliances, near-infrared radiation coming from outside need to be blocked.

In addition, there is a problem that a near-infrared light emitted from a plasma display acts on its surrounding electric appliances that utilizes near-infrared remote control, such as a cordless phone and a video tape recorder, to cause malfunction. Therefore, there is a demand for a plasma display filter that exerts a near-infrared absorbing effect.

Furthermore, recently, reading of information signals such as bar codes is increasingly performed using a near-infrared light so as to prevent malfunction, ensure the security and make printed matters such as bar codes inconspicuous, and near-infrared absorbing inks and the like are used therein.

In the near-infrared absorbing materials used in these applications, conventionally, near-infrared absorbing pigments that absorb near-infrared radiation, such as cyanine-based pigments, phthalocyanine-based pigments, polymethine-based pigments, squarylium-based pigments, porphyrin-based pigments, metal dithiol complex-based pigments, diimonium-based pigments and inorganic oxide particles, have been employed (Patent Document 1).

However, when these near-infrared absorbing pigments are used as near-infrared absorbing materials, they are often used in combination with a synthetic resin such as a thermoplastic resin and, in such cases, there is a problem in the compatibility with the resin, and the pigments have an absorption wavelength in the visible light region and thus often impair the transparency and other physical properties of the resin. In addition, since these near-infrared absorbing pigments have a narrow absorption spectral width and do not show sufficient near-infrared light shielding effect, their near-infrared absorbing capacities are not satisfactory. Particularly, there is a demand for a material that shows efficient absorption in the near-infrared region.

Meanwhile, in the compound described in Patent Document 2, an alkoxy group is not essential in the phthalocyanine-constituting ring and an image-forming toner is the intended use of the compound; therefore, the findings of the present invention cannot be obtained.

RELATED ART DOCUMENTS

Patent Documents

Patent Document 1: Japanese Unexamined Patent Application Publication No. 2010-197305
Patent Document 2: Japanese Unexamined Patent Application Publication No. 2007-316255

SUMMARY OF THE INVENTION

Problems to be Solved by the Invention

Therefore, an object of the present invention is to provide a near-infrared absorbing agent and a near-infrared absorbing composition, which have excellent near-infrared absorbing capacity; a near-infrared absorbing resin composition in which the physical properties intrinsic to a resin are not impaired; and a near-infrared absorbing material having excellent near-infrared absorbing capacity.

Means for Solving the Problems

In order to solve the above-described problems, the present inventors intensively studied and focused on a composition comprising a specific phthalocyanine compound, thereby completing the present invention.

That is, the near-infrared absorbing agent of the present invention comprises a phthalocyanine compound represented by the following Formula (1):

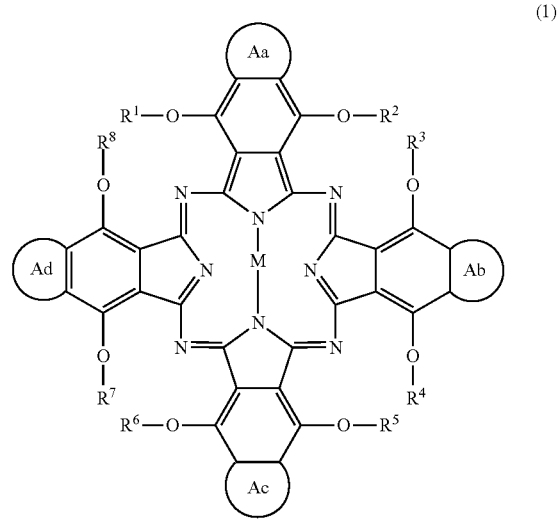

(wherein, M represents two hydrogen atoms, a divalent metal atom, a trivalent substituted metal atom, a tetravalent substituted metal atom, or an oxymetal atom; $R^1$ to $R^8$ may be the same or different from each other and each represent an alkyl group having 1 to 20 carbon atoms which is optionally substituted, an aryl group having 6 to 20 carbon atoms which is optionally substituted, an arylalkyl group having 7 to 20 carbon atoms which is optionally substituted, or a cycloalkyl group having 5 to 12 carbon atoms which is optionally substituted; and Aa, Ab, Ac and Ad each independently represent a cyclic structure represented by the following Formula (2), (3) or (4), with a proviso that at least one, but not all, of the Aa, Ab, Ac and Ad is the cyclic structure represented by the Formula (4))

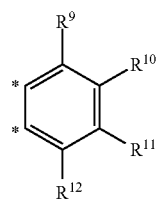

(2)

(wherein, $R^9$ to $R^{12}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and the Formula (2) is bound to the Formula (1) at * positions)

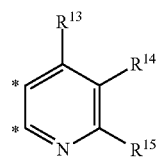

(3)

(wherein, $R^{13}$ to $R^{15}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and the Formula (3) is bound to the Formula (1) at * positions)

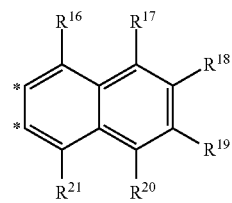

(4)

(wherein, $R^{16}$ to $R^{21}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and the Formula (4) is bound to the Formula (1) at * positions).

The near-infrared absorbing composition of the present invention comprises at least one near-infrared absorbing agent described above.

The near-infrared absorbing material of the present invention comprises at least one above-described near-infrared absorbing agent described above.

The near-infrared absorbing resin composition of the present invention comprises the above-described near-infrared absorbing agent and a synthetic resin.

In the near-infrared absorbing resin composition of the present invention, it is preferred that the total content of the phthalocyanine compound represented by the Formula (1) be 0.0005 to 20 parts by mass with respect to 100 parts by mass of the synthetic resin. In the near-infrared absorbing resin composition of the present invention, it is also preferred that the synthetic resin be a thermoplastic resin.

The near-infrared absorbing material of the present invention is obtained by molding the above-described near-infrared absorbing resin composition.

Effects of the Invention

According to the present invention, a near-infrared absorbing agent and a near-infrared absorbing composition, which have excellent near-infrared absorbing capacity, can be provided. In addition, a near-infrared absorbing resin composition in which the physical properties intrinsic to a resin are not impaired can be provided. Furthermore, a near-infrared absorbing material that is obtained by molding the near-infrared absorbing resin composition and has excellent near-infrared absorbing capacity as well as excellent intrinsic physical properties of a resin can also be provided.

BRIEF DESCRIPTION OF THE DRAWINGS

FIG. 1 shows an NMR chart of the composition obtained in Synthesis Example 1.

FIG. 2 shows an NMR chart of the composition obtained in Synthesis Example 2.

FIG. 3 shows an NMR chart of the composition obtained in Synthesis Example 3.

FIG. 4 shows absorption spectra of the compositions obtained in Synthesis Examples 1 to 3 and Comparative Synthesis Example 1.

FIG. 5 shows absorption spectra of the compositions obtained in Synthesis Examples 4 and 5.

FIG. 6 shows an absorption spectrum of the test piece of Example 1.

MODE FOR CARRYING OUT THE INVENTION

The present invention will now be described in detail.

First, the near-infrared absorbing agent and the near-infrared absorbing composition of the present invention will be described. The near-infrared absorbing agent of the present invention comprises a phthalocyanine compound represented by the following Formula (1). The near-infrared absorbing composition of the present invention comprises at least one phthalocyanine compound represented by the following Formula (1):

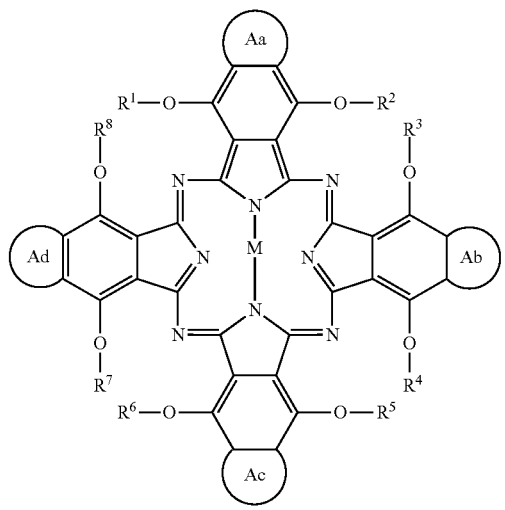

(1)

(wherein, M represents two hydrogen atoms, a divalent metal atom, a trivalent substituted metal atom, a tetravalent substituted metal atom, or an oxymetal atom; $R^1$ to $R^8$ may be the same or different from each other and each represent an alkyl group having 1 to 20 carbon atoms which is optionally substituted, an aryl group having 6 to 20 carbon atoms which is optionally substituted, an arylalkyl group having 7 to 20 carbon atoms which is optionally substituted, or a cycloalkyl group having 5 to 12 carbon atoms which is optionally substituted; and Aa, Ab, Ac and Ad each independently represent a cyclic structure represented by the following Formula (2), (3) or (4), with a proviso that at least one, but not all, of the Aa, Ab, Ac and Ad is the cyclic structure represented by said Formula (4))

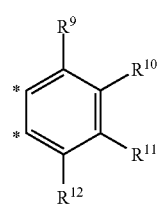

(2)

(wherein, $R^9$ to $R^{12}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and the Formula (2) is bound to the Formula (1) at * positions)

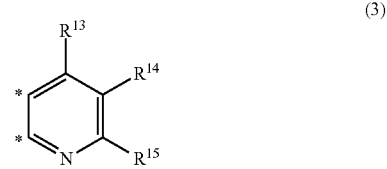

(3)

(wherein, $R^{13}$ to $R^{15}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and the Formula (3) is bound to the Formula (1) at * positions)

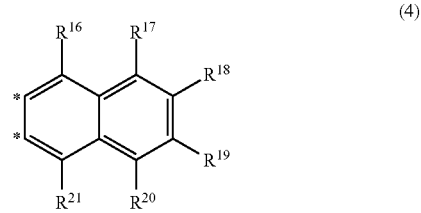

(4)

(wherein, $R^{16}$ to $R^{21}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and the Formula (4) is bound to the Formula (1) at * positions).

In the Formula (1), M represents two hydrogen atoms, a divalent metal atom, a trivalent substituted metal atom, a tetravalent substituted metal atom, or an oxymetal atom.

Examples of the divalent metal atom include Cu, Zn, Fe, Co, Ni, Ru, Rh, Pd, Pt, Mn, Mg, Ti, Be, Ca, Ba, Cd, Hg, Pb and Sn.

Examples of the trivalent substituted metal atom include mono-substituted trivalent metal atoms, such as AlCl, AlBr, AlF, AlI, GaCl, GaF, GaI, GaBr, InCl, InBr, InI, InF, TlCl, TlBr, TlI, TlF, FeCl, RuCl, Al—$C_6H_5$, Al—$C_6H_4(CH_3)$, In—C$_6$H$_5$, In—C$_6$H$_4$(CH$_3$), In—C$_6$H$_5$, Al(OH), Mn(OH), Mn(OC$_6$H$_5$) and Mn[OSi(CH$_3$)$_3$].

Examples of the tetravalent substituted metal atom include di-substituted tetravalent metal atoms, such as CrCl$_2$, SiCl$_2$, SiBr$_2$, SiF$_2$, SiI$_2$, ZrCl$_2$, GeCl$_2$, GeBr$_2$, GeI$_2$, GeF$_2$, SnCl$_2$, SnBr$_2$, SnF$_2$, TiCl$_2$, TiBr$_2$, TiF$_2$, Si(OH)$_2$, Ge(OH)$_2$, Zr(OH)$_2$, Mn(OH)$_2$ and Sn(OH)$_2$; TiR$_2$, CrR$_2$, SiR$_2$, SnR$_2$ and GeR$_2$ (wherein, R represents an alkyl group, a phenyl group, a naphthyl group, or a derivative thereof); Si(OR')$_2$, Sn(OR')$_2$, Ge(OR')$_2$, Ti(OR')$_2$ and Cr(OR')$_2$ (wherein, R' represents an alkyl group, a phenyl group, a naphthyl group, a trialkylsilyl group, a dialkylalkoxysilyl group, or a derivative thereof); and Sn(SR")$_2$ and Ge(SR")$_2$ (wherein, R" represents an alkyl group, a phenyl group, a naphthyl group, or a derivative thereof).

Examples of the oxymetal atom include VO, MnO and TiO.

Thereamong, from the standpoints of the near-infrared absorbing capacity and the stability, M is preferably two hydrogen atoms, or a divalent Cu, Ni or VO.

Examples of the alkyl group having 1 to 20 carbon atoms which is optionally substituted and represented by R$^1$ to R$^8$ in the Formula (1) include unsubstituted alkyl groups having 1 to 20 carbon atoms, such as methyl, ethyl, n-propyl, isopropyl, n-butyl, isobutyl, sec-butyl, tert-butyl, n-pentyl, isopentyl, neopentyl, tert-amyl, 1,2-dimethylpropyl, n-hexyl, cyclohexyl, 1,3-dimethylbutyl, 1-isopropylpropyl, 1,2-dimethylbutyl, n-heptyl, 2-heptyl, 1,4-dimethylpentyl, tert-heptyl, 2-methyl-1-isopropylpropyl, 1-ethyl-3-methylbutyl, n-octyl, tert-octyl, 2-ethylhexyl, 2-methylhexyl, 2-propylhexyl, n-nonyl, isononyl, n-decyl, isodecyl, n-undecyl, isoundecyl, n-dodecyl, isododecyl, n-tridecyl, isotridecyl, n-tetradecyl, isotetradecyl, n-pentadecyl, isopentadecyl, n-hexadecyl, isohexadecyl, n-heptadecyl, isoheptadecyl, n-octadecyl, isooctadecyl, n-nonadecyl, isononadecyl, n-icosyl and isoicosyl.

Examples of the aryl group having 6 to 20 carbon atoms which is optionally substituted and represented by R$^1$ to R$^8$ in the Formula (1) include phenyl, naphthyl, anthracen-1-yl and phenanthren-1-yl.

Examples of the arylalkyl group having 7 to 20 carbon atoms which is optionally substituted and represented by R$^1$ to R$^8$ in the Formula (1) include benzyl, phenethyl, 2-phenylpropan-2-yl, styryl, cinnamyl, diphenylmethyl and triphenylmethyl.

Examples of the cycloalkyl group having 5 to 12 carbon atoms which is optionally substituted and represented by R$^1$ to R$^8$ in the Formula (1) include cyclopentyl, cyclohexyl, cyclooctyl, cyclododecyl and 4-methylcyclohexyl.

In the above-described alkyl group having 1 to 20 carbon atoms which is optionally substituted, aryl group having 6 to 20 carbon atoms which is optionally substituted, arylalkyl group having 7 to 20 carbon atoms which is optionally substituted and cycloalkyl group having 5 to 12 carbon atoms which is optionally substituted, all of which are represented by R$^1$ to R$^8$, examples of a substituent include alkyl groups such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl and decyl; alkoxy groups such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy and decyloxy; amylthio groups such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio and 2-ethylhexylthio; alkenyl groups such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl and tricosenyl; arylalkyl groups such as benzyl, phenethyl, diphenylmethyl, triphenylmethyl, styryl and cinnamyl; aryl groups such as phenyl and naphthyl; aryloxy groups such as phenoxy and naphthyloxy; arylthio groups such as phenylthio and naphthylthio; heterocyclic groups such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl and 2,4-dioxyoxazolidin-3-yl; halogen atoms such as fluorine, chlorine, bromine and iodine; acyl groups such as acetyl, 2-chloroacetyl, propionyl, octanoyl, acryloyl, methacryloyl, phenylcarbonyl(benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl and carbamoyl; acyloxy groups such as acetyloxy and benzoyloxy; substituted amino groups such as amino, ethylamino, dimethylamino, diethylamino, butylamino, cyclopentylamino, 2-ethylhexylamino, dodecylamino, anilino, chlorophenylamino, toluidino, anisidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino and phenylsulfonylamino; a sulfonamide group; a sulfonyl group; a carboxyl group; a cyano group; a sulfo group; a hydroxyl group; a nitro group; a mercapto group; an imide group; and a carbamoyl group, and these groups may further be substituted as well. Moreover, the carboxyl group and the sulfo group may each form a salt. In cases where the alkyl group having 1 to 20 carbon atoms, the aryl group having 6 to 20 carbon atoms, the arylalkyl group having 7 to 20 carbon atoms and the cycloalkyl group having 5 to 12 carbon atoms have a carbon atom-containing substituent(s), the number of the carbon atoms including the carbon atoms contained in the substituent(s) is controlled to be in the respective prescribed ranges.

From the standpoints of the near-infrared absorbing capacity and the stability, R$^1$ to R$^8$ are each preferably an alkyl group having 1 to 20 carbon atoms which is optionally substituted, more preferably an unsubstituted alkyl group having 1 to 8 carbon atoms.

Examples of the halogen atom represented by R$^9$ to R$^{12}$ in the Formula (2) include fluorine, chlorine, bromine and iodine.

Examples of the alkyl group having 1 to 20 carbon atoms which is optionally substituted and represented by R$^9$ to R$^{12}$ in the Formula (2) include the same alkyl groups as those exemplified above.

Examples of the aryl group having 6 to 20 carbon atoms which is optionally substituted and represented by $R^9$ to $R^{12}$ in the Formula (2) include the same aryl groups as those exemplified above.

Examples of the alkoxy group having 1 to 20 carbon atoms which is optionally substituted and represented by $R^9$ to $R^{12}$ in the Formula (2) include those alkoxy groups that correspond to the alkyl groups exemplified above, specifically methoxy, ethoxy, n-propoxy, isopropoxy, n-butoxy, isobutoxy, sec-butoxy, tert-butoxy, n-pentyloxy, isopentyloxy, neopentyloxy, 1,2-dimethyl-propoxy, n-hexyloxy, cyclohexyloxy, 1,3-dimethylbutoxy and 1-isopropyl-propoxy. Examples of a substituent in this case include the same ones as those exemplified above.

Examples of the aryloxy group having 6 to 20 carbon atoms which is optionally substituted and represented by $R^9$ to $R^{12}$ in the Formula (2) include those aryloxy groups that correspond to the aryl groups exemplified above, specifically phenoxy and naphthoxy. Examples of a substituent in this case include the same ones as those exemplified above.

Examples of the arylalkyl group having 7 to 20 carbon atoms which is optionally substituted and represented by $R^9$ to $R^{12}$ in the Formula (2) include the same arylalkyl groups as those exemplified above.

Examples of the cycloalkyl group having 5 to 12 carbon atoms which is optionally substituted and represented by $R^9$ to $R^{12}$ in the Formula (2) include the same cycloalkyl groups as those exemplified above.

From the standpoints of the near-infrared absorbing capacity and the stability, $R^9$ to $R^{12}$ are each preferably a hydrogen atom, a halogen atom, or an unsubstituted alkyl group having 1 to 8 carbon atoms.

Examples of the halogen atom represented by $R^{13}$ to $R^{15}$ in the Formula (3) include fluorine, chlorine, bromine and iodine.

Examples of the alkyl group having 1 to 20 carbon atoms which is optionally substituted and represented by $R^{13}$ to $R^{15}$ in the Formula (3) include the same alkyl groups as those exemplified above.

Examples of the aryl group having 6 to 20 carbon atoms which is optionally substituted and represented by $R^{13}$ to $R^{15}$ in the Formula (3) include the same aryl groups as those exemplified above.

Examples of the alkoxy group having 1 to 20 carbon atoms which is optionally substituted and represented by $R^{13}$ to $R^{15}$ in the Formula (3) include the same alkoxy groups as those exemplified above.

Examples of the aryloxy group having 6 to 20 carbon atoms which is optionally substituted and represented by $R^{13}$ to $R^{15}$ in the Formula (3) include the same aryloxy groups as those exemplified above.

Examples of the arylalkyl group having 7 to 20 carbon atoms which is optionally substituted and represented by $R^{13}$ to $R^{15}$ in the Formula (3) include the same arylalkyl groups as those exemplified above.

Examples of the cycloalkyl group having 5 to 12 carbon atoms which is optionally substituted and represented by $R^{13}$ to $R^{15}$ in the Formula (3) include the same cycloalkyl groups as those exemplified above.

From the standpoints of the near-infrared absorbing capacity and the stability, $R^{13}$ to $R^{15}$ are each preferably a hydrogen atom, a halogen atom, or an unsubstituted alkyl group having 1 to 8 carbon atoms.

Examples of the halogen atom represented by $R^{16}$ to $R^{21}$ in the Formula (4) include fluorine, chlorine, bromine and iodine.

Examples of the alkyl group having 1 to 20 carbon atoms which is optionally substituted and represented by $R^{16}$ to $R^{21}$ in the Formula (4) include the same alkyl groups as those exemplified above.

Examples of the aryl group having 6 to 20 carbon atoms which is optionally substituted and represented by $R^{16}$ to $R^{21}$ in the Formula (4) include the same aryl groups as those exemplified above.

Examples of the alkoxy group having 1 to 20 carbon atoms which is optionally substituted and represented by $R^{16}$ to $R^{21}$ in the Formula (4) include the same alkoxy groups as those exemplified above.

Examples of the aryloxy group having 6 to 20 carbon atoms which is optionally substituted and represented by $R^{16}$ to $R^{21}$ in the Formula (4) include the same aryloxy groups as those exemplified above.

Examples of the arylalkyl group having 7 to 20 carbon atoms which is optionally substituted and represented by $R^{16}$ to $R^{21}$ in the Formula (4) include the same arylalkyl groups as those exemplified above.

Examples of the cycloalkyl group having 5 to 12 carbon atoms which is optionally substituted and represented by $R^{16}$ to $R^{21}$ in the Formula (4) include the same cycloalkyl groups as those exemplified above.

From the standpoints of the near-infrared absorbing capacity and the stability, $R^{16}$ to $R^{21}$ are each preferably a hydrogen atom, a halogen atom, or an unsubstituted alkyl group having 1 to 8 carbon atoms.

Specific examples of the phthalocyanine compound which is represented by the above-described Formula (1) and contained in the near-infrared absorbing composition of the present invention include, but not limited to, the following Compounds No. 1 to No. 46. It is noted here that Bu represents a butyl group and Me represents a methyl group.

Compound No. 1

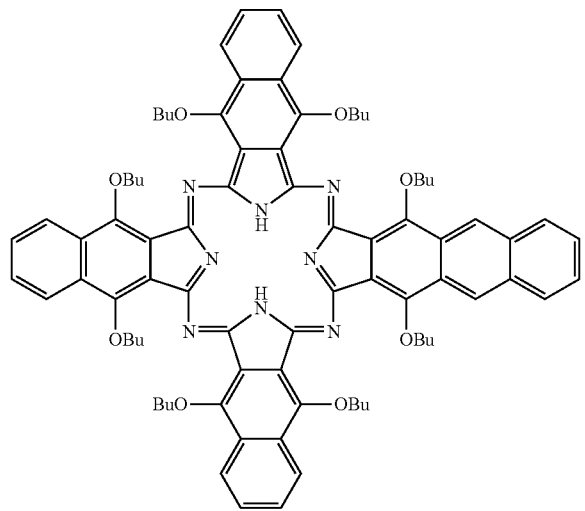

Compound No. 2
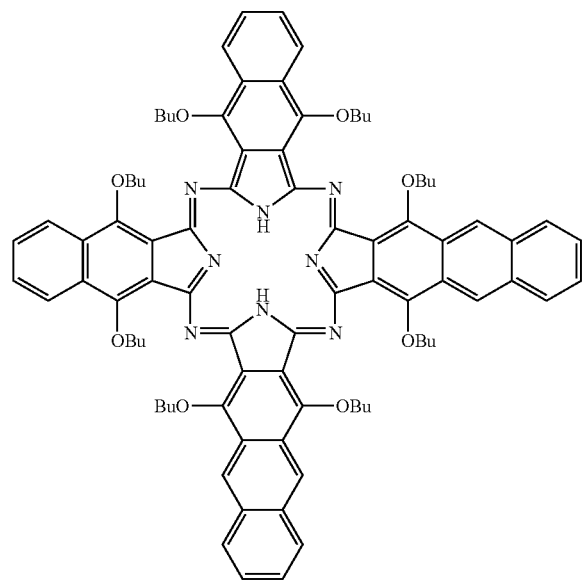
Compound No. 3
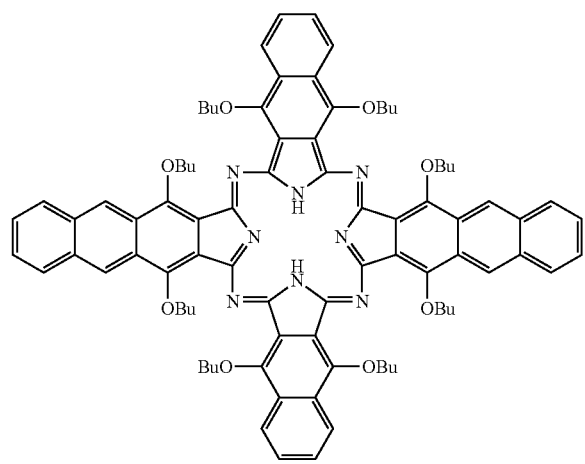
Compound No. 4
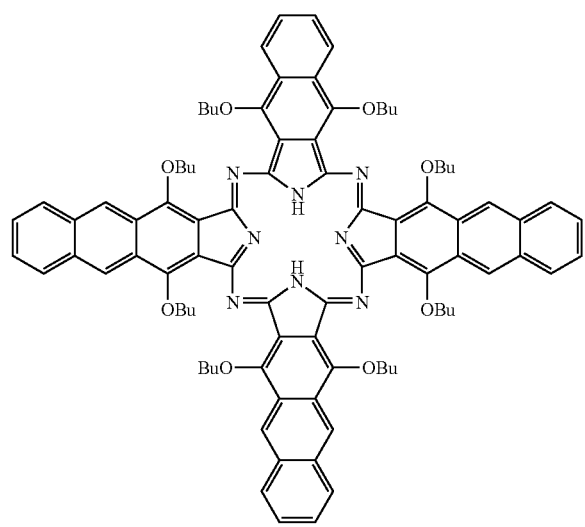
Compound No. 5
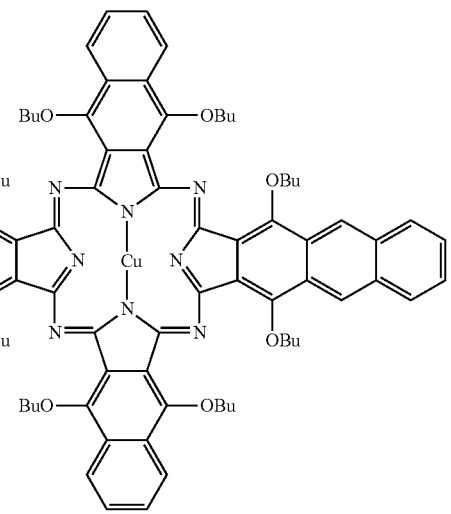
Compound No. 6
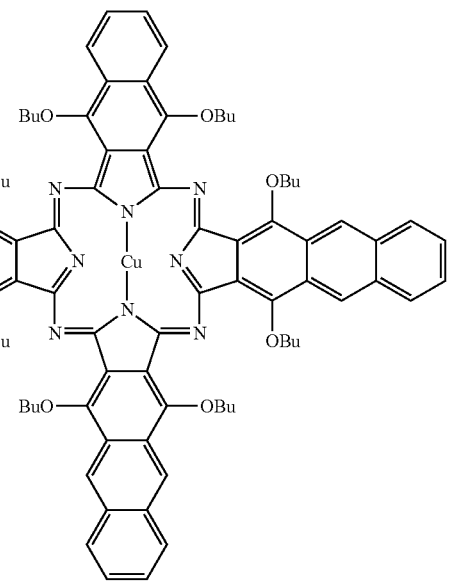
Compound No. 7
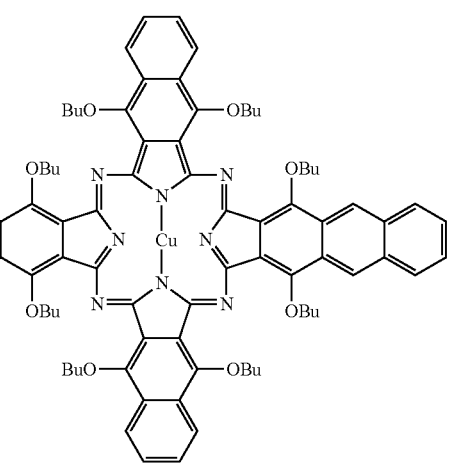

-continued
Compound No. 8
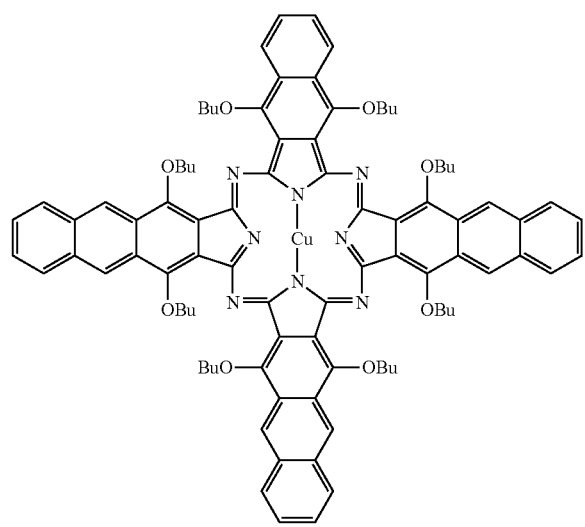
Compound No. 9
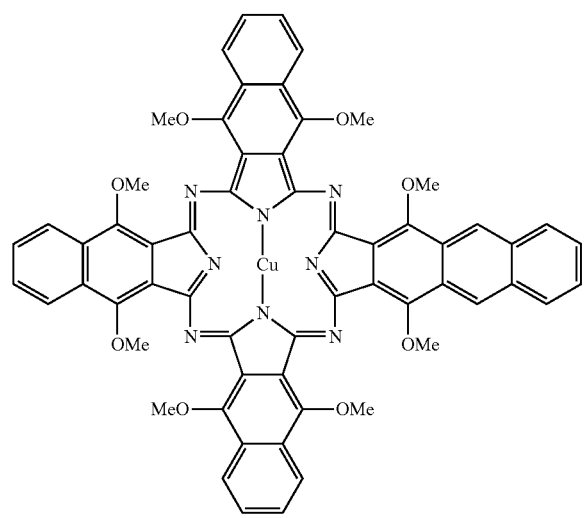
Compound No. 10
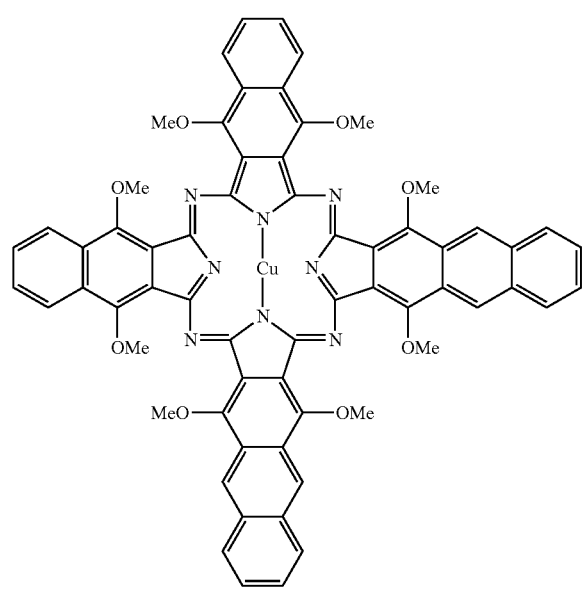
-continued
Compound No. 11
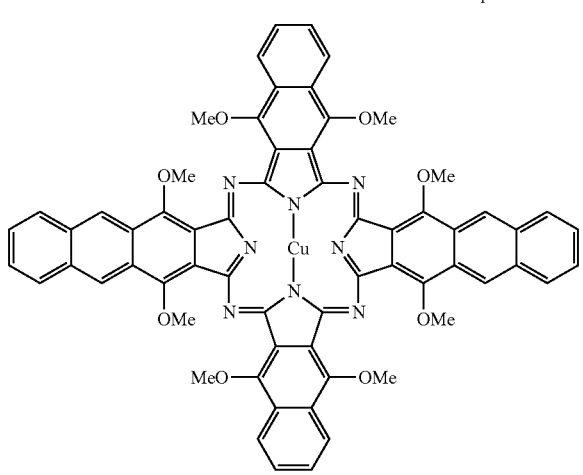
Compound No. 12
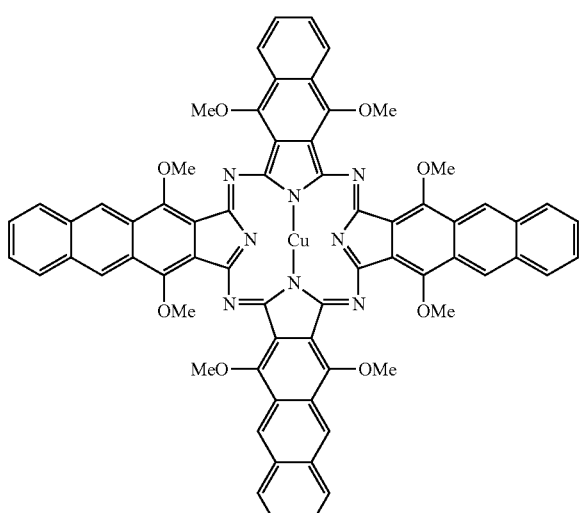
Compound No. 13
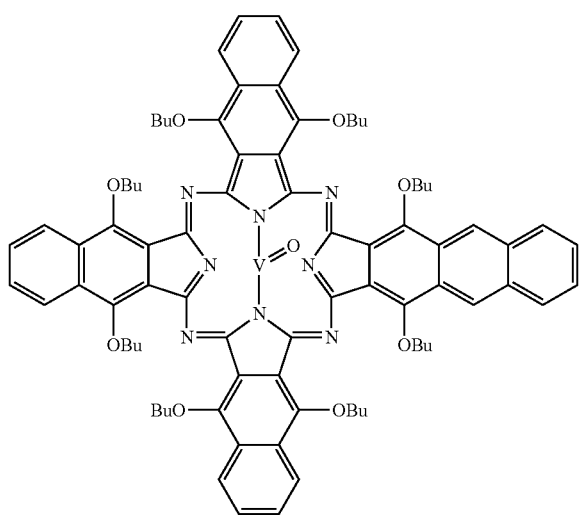

Compound No. 14
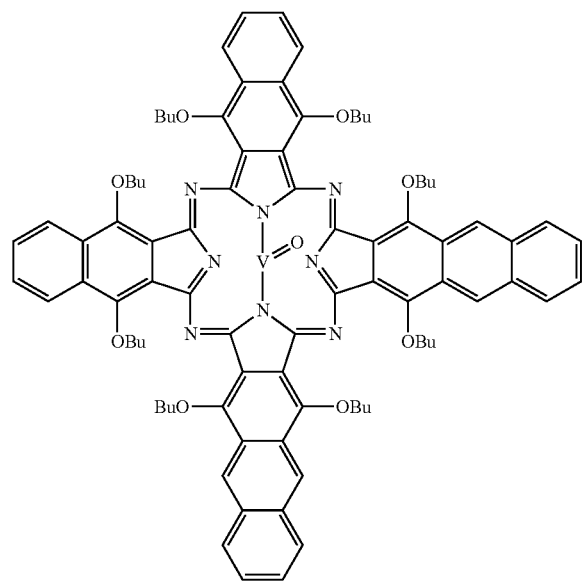
Compound No. 15
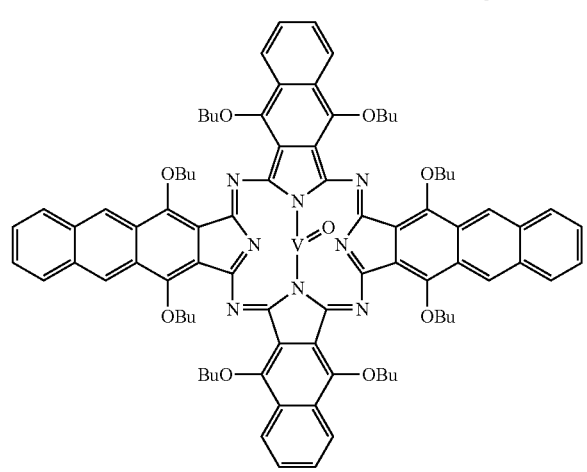
Compound No. 16
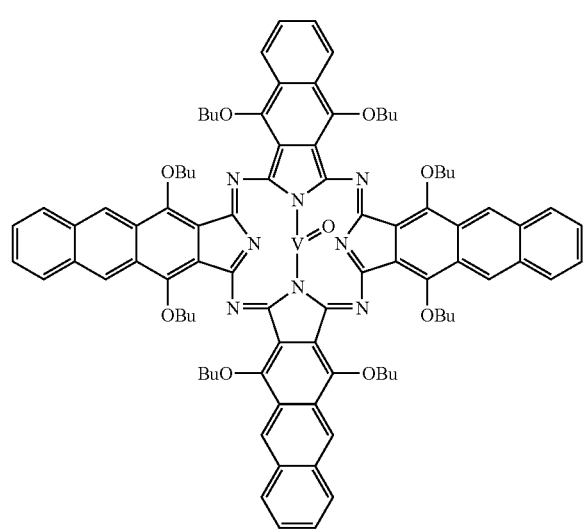
Compound No. 17
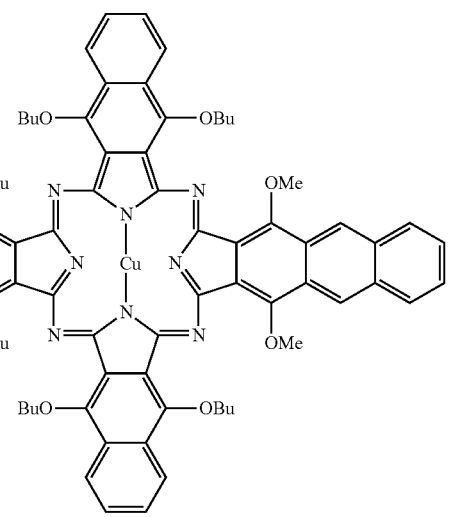
Compound No. 18
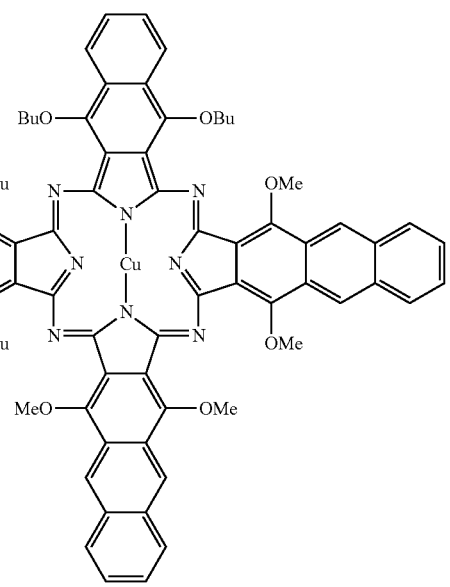
Compound No. 19
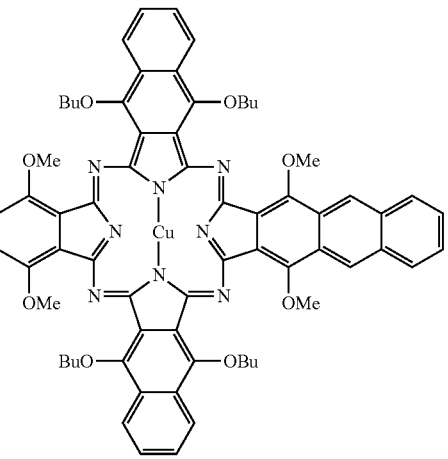

-continued
Compound No. 20
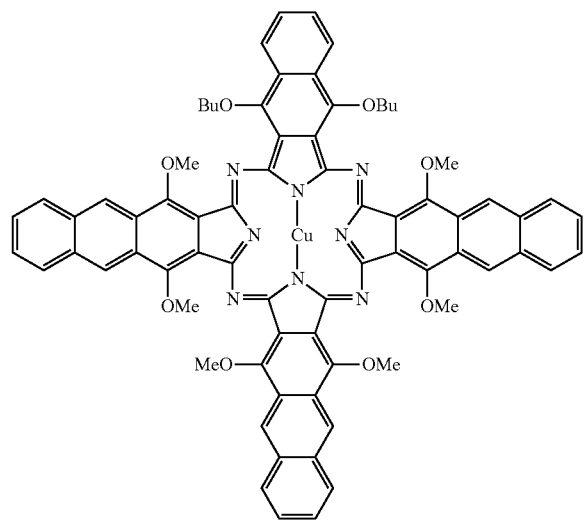
Compound No.21
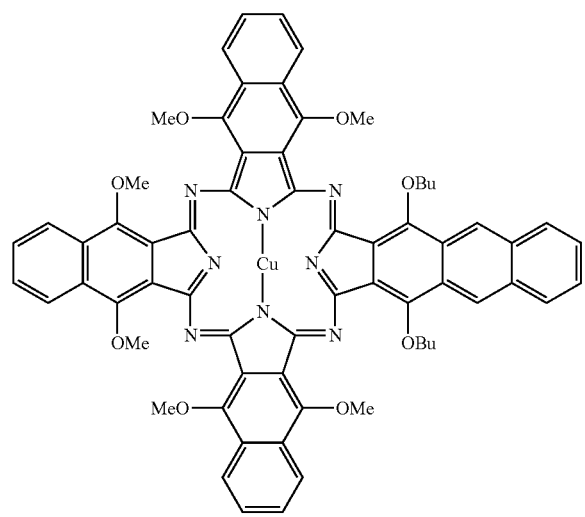
Compound No. 22
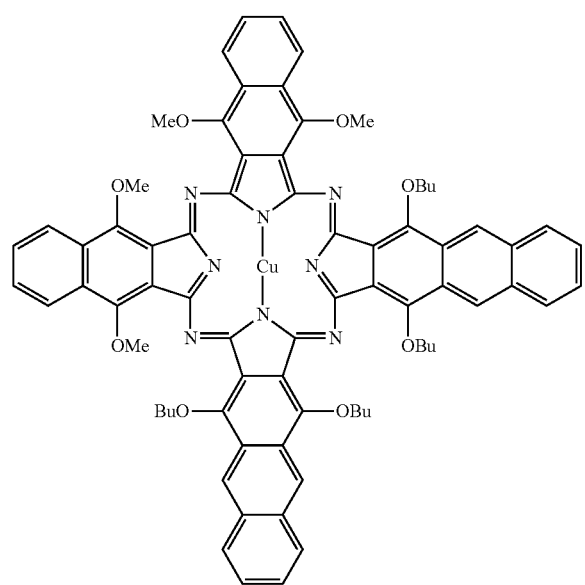
Compound No. 23
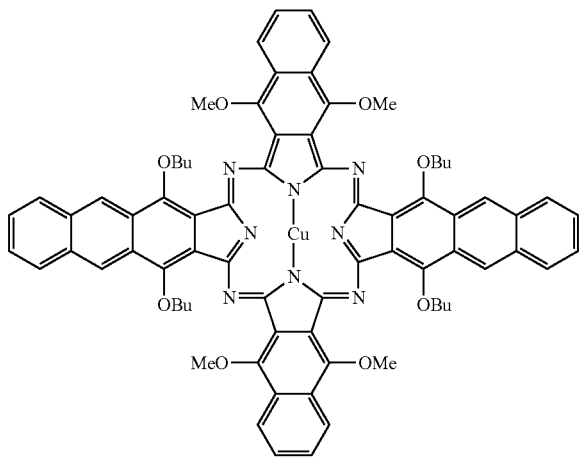
Compound No. 24
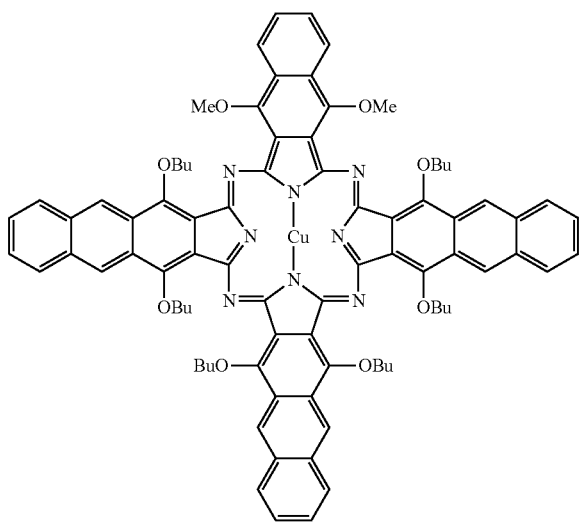
Compound No. 25
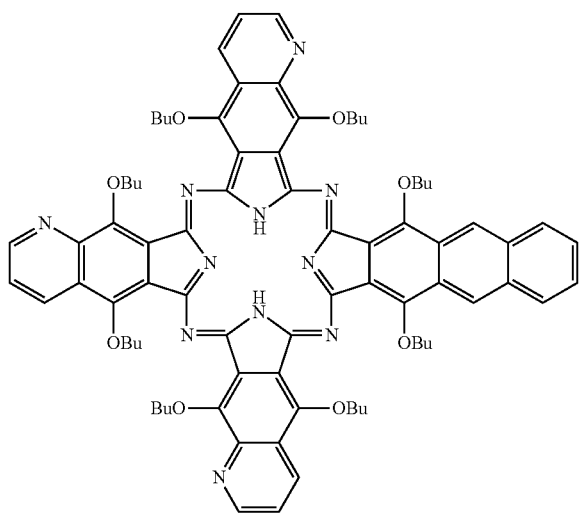

Compound No. 26
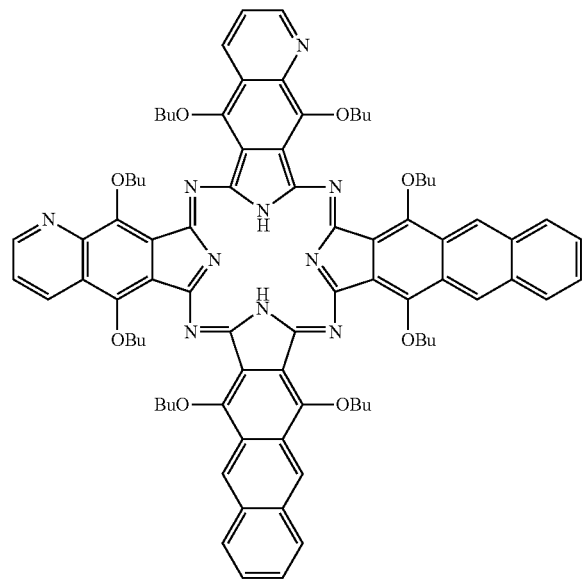
Compound No. 27
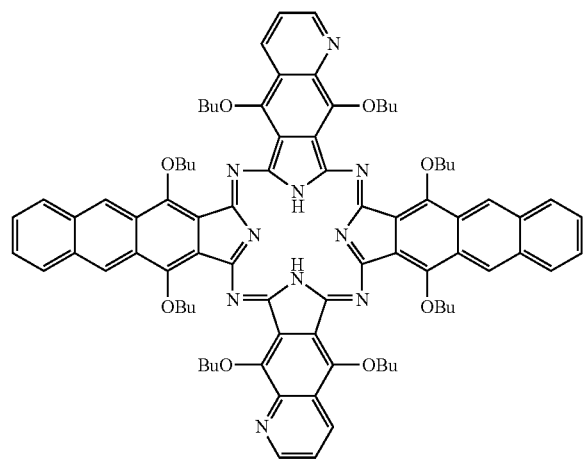
Compound No. 28
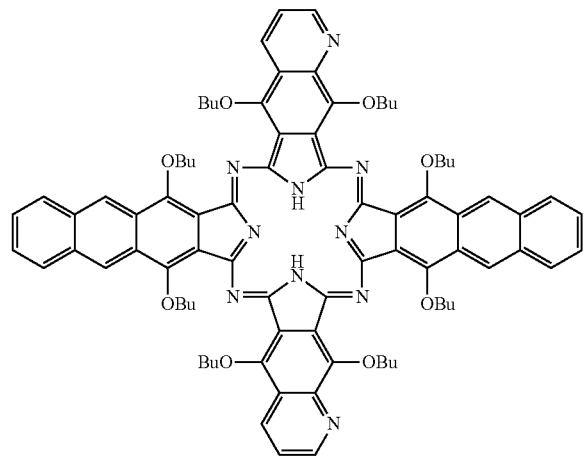
Compound No. 29
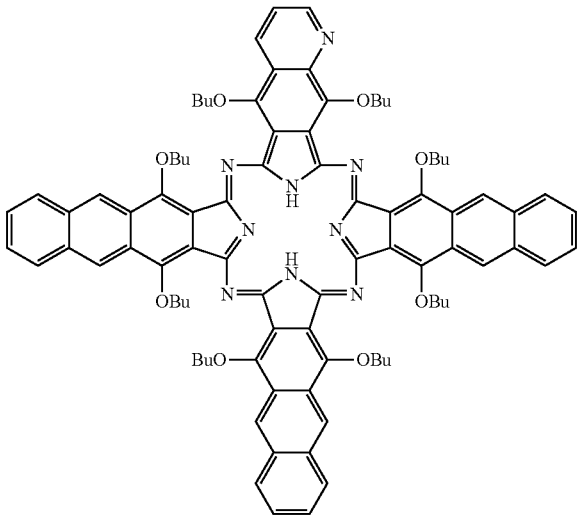
Compound No. 30
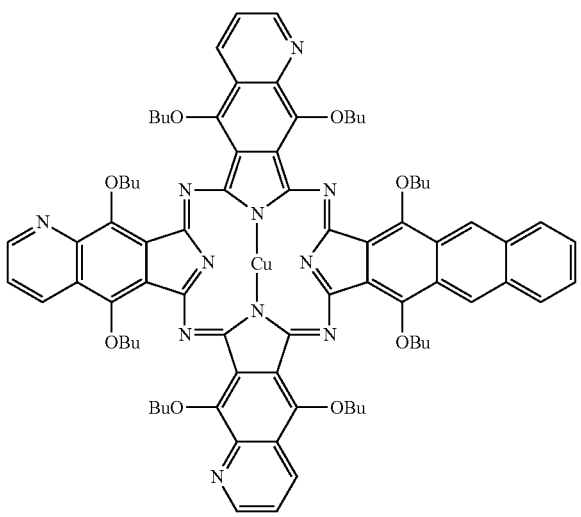
Compound No. 31
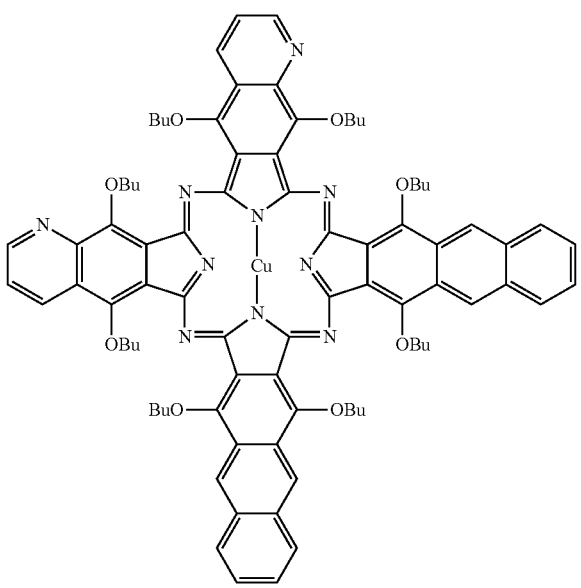

Compound No. 32
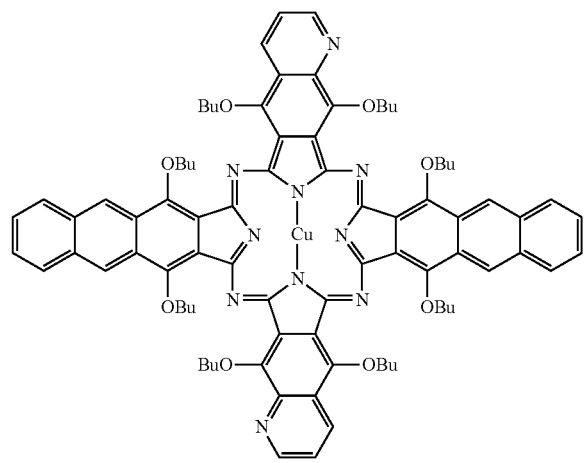
Compound No. 33
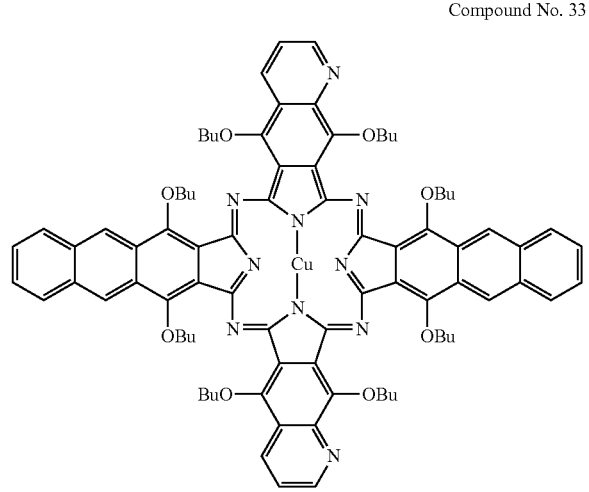
Compound No. 34
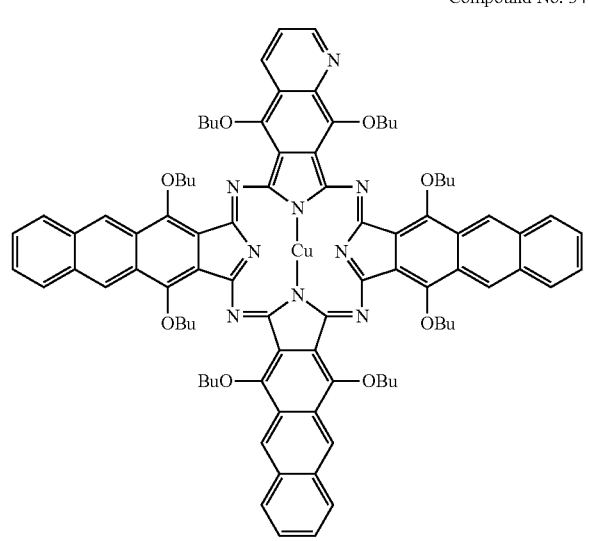
Compound No. 35
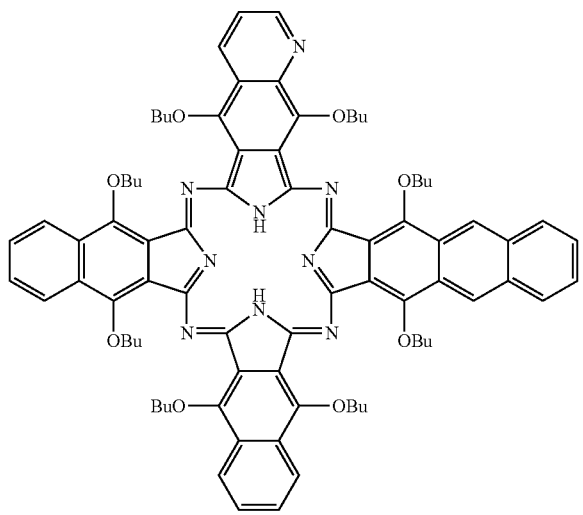
Compound No. 36
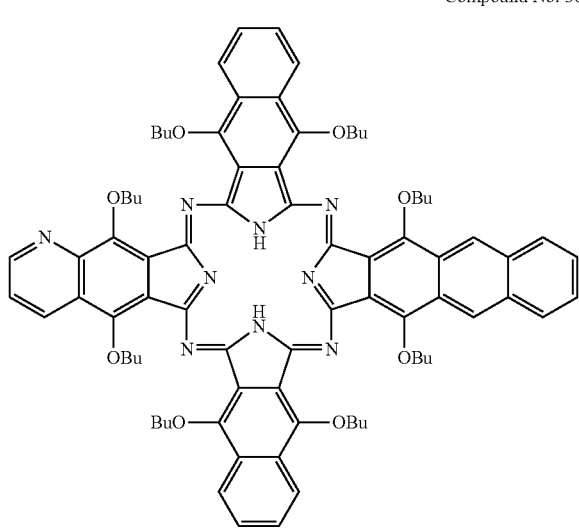
Compound No. 37
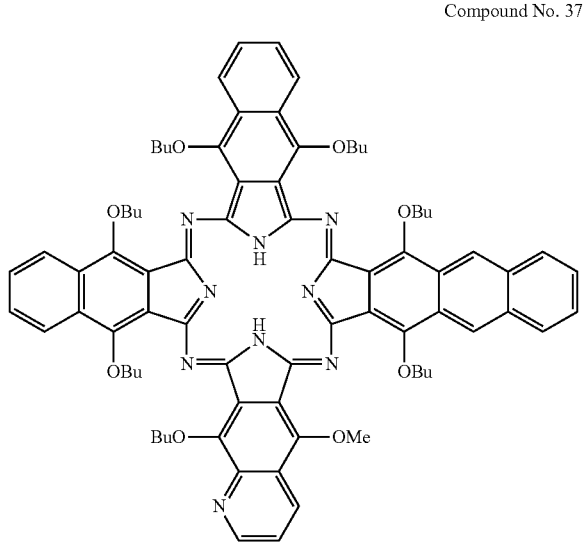

Compound No. 38
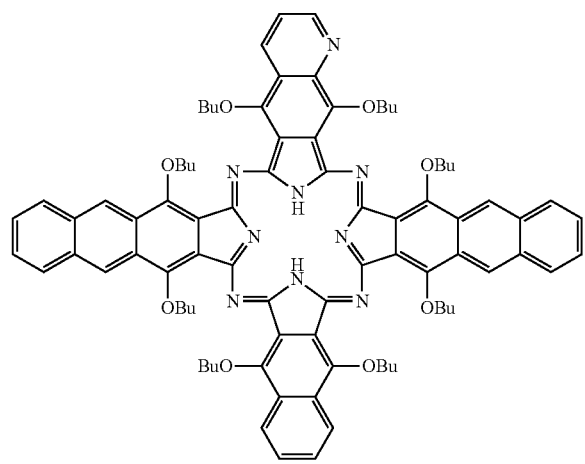
Compound No. 39
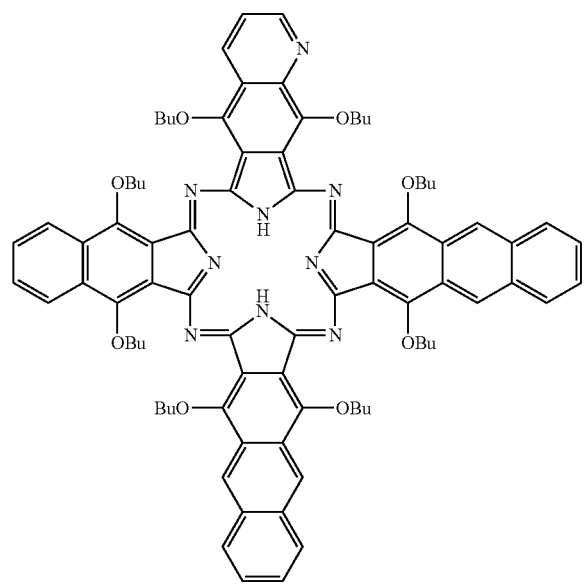
Compound No. 40
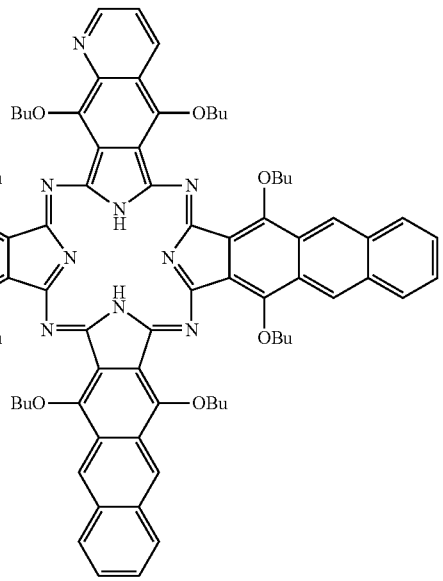
Compound No. 41
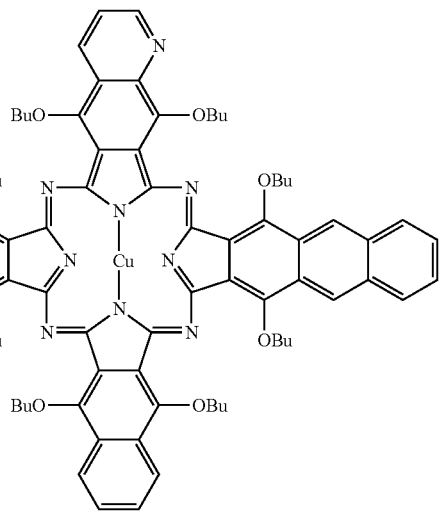
Compound No. 42
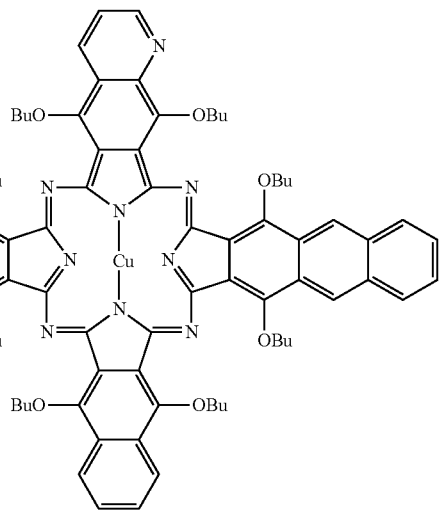

Compound No. 43

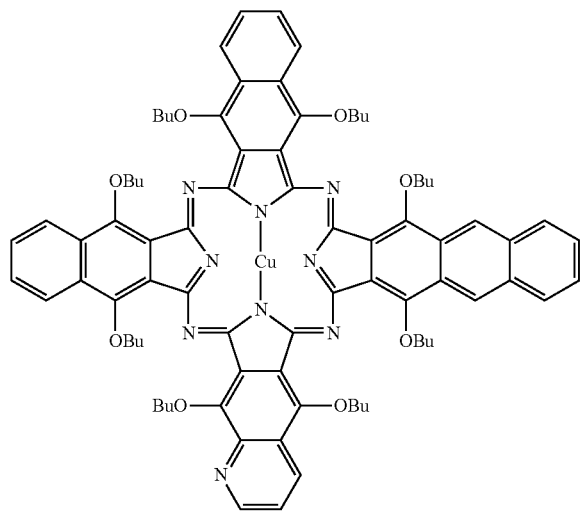

Compound No. 44

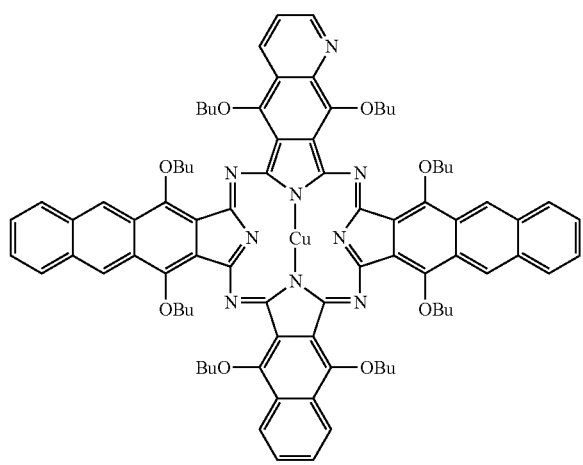

Compound No. 45

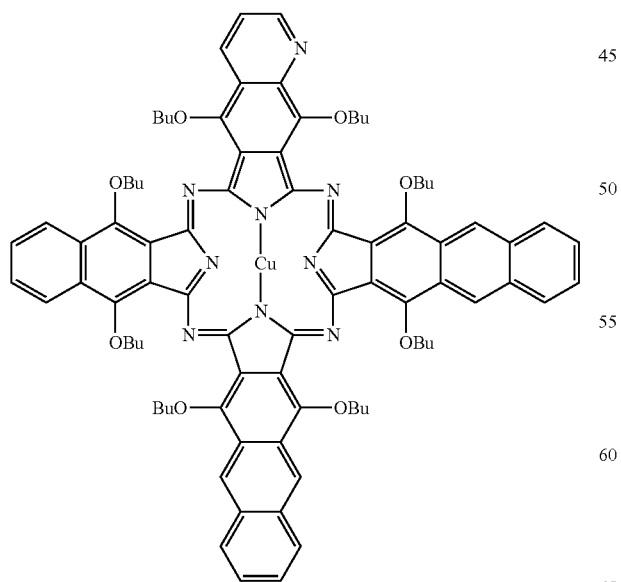

Compound No. 46

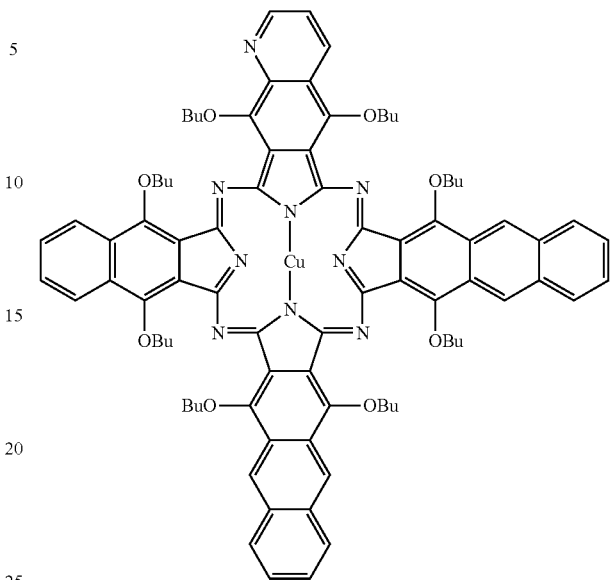

The phthalocyanine compound represented by the Formula (1) can be produced by applying a conventionally known reaction. For example, the phthalocyanine compound can be synthesized by a conventional method using, as raw materials, at least one dicyanonaphthalene compound represented by the below-described Formula (5) or (6) and at least one dicyanoanthracene compound represented by the below-described Formula (7).

Further, by changing the ratio of the dicyanonaphthalene compound(s) represented by the Formula (5) or (6) and the dicyanoanthracene compound(s) represented by the Formula (7), which are the raw materials, one or more compounds represented by the Formula (1) can be synthesized simultaneously, and it is also preferred to use a mixture thereof as the near-infrared absorbing composition of the present invention.

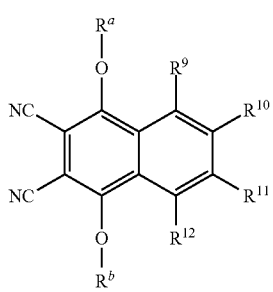

(5)

In the Formula (5), $R^a$ corresponds to any one of $R^1$, $R^2$, $R^3$, $R^4$, $R^5$, $R^6$, $R^7$ and $R^8$ of the Formula (1); $R^b$ corresponds to any one of $R^1$, $R^2$, $R^3$, $R^4$, $R^5$, $R^6$, $R^7$ and $R^8$ of the Formula (1); and $R^9$, $R^{10}$, $R^{11}$ and $R^{12}$ each correspond to the Formula (2).

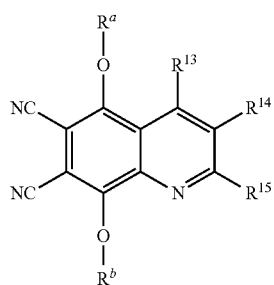

(6)

In the Formula (6), $R^a$ corresponds to any one of $R^1$, $R^2$, $R^3$, $R^4$, $R^5$, $R^6$, $R^7$ and $R^8$ of the Formula (1); $R^b$ corresponds to any one of $R^1$, $R^2$, $R^3$, $R^4$, $R^5$, $R^6$, $R^7$ and $R^8$ of the Formula (1); and $R^{13}$, $R^{14}$ and $R^{15}$ each correspond to the Formula (3).

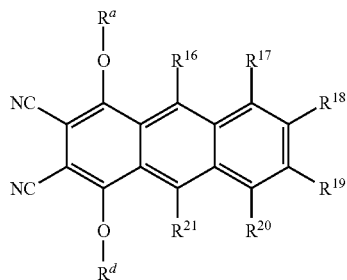

(7)

In the Formula (7), $R^c$ corresponds to any one of $R^1$, $R^2$, $R^3$, $R^4$, $R^5$, $R^6$, $R^7$ and $R^8$ of the Formula (1); $R^d$ corresponds to any one of $R^1$, $R^2$, $R^3$, $R^4$, $R^5$, $R^6$, $R^7$ and $R^8$ of the Formula (1); and $R^{16}$, $R^{17}$, $R^{18}$, $R^{19}$, $R^{20}$ and $R^{21}$ each correspond to the Formula (4).

The near-infrared absorbing agent and the near-infrared absorbing composition of the present invention can be used in a variety of applications as a near-infrared absorbing material by, directly or in combination with a binder resin and/or an additive(s), applying to or kneading with a paper, a plastic sheet, a plastic, a film, a glass, a resin or the like, coating, or polymerizing a mixture thereof with a monomer.

Particularly, the near-infrared absorbing agent or the near-infrared absorbing composition of the present invention that is, for example, mixed with or dispersed in a resin is preferably used as a near-infrared absorbing resin composition. Such a near-infrared absorbing resin composition can be used as a near-infrared absorbing material such as a resin glass, an automobile interior or exterior material, a glazing application, a near-infrared absorbing filter, a plasma display filter, an agricultural film, a heat ray-shielding film, an anti-counterfeit printing ink or a light-receiving element.

A method of producing a near-infrared absorbing material using the near-infrared absorbing agent or the near-infrared absorbing composition of the present invention is not particularly restricted and, for example, any of the following three methods can be employed:

(1) a method in which the near-infrared absorbing agent or the near-infrared absorbing composition of the present invention is blended and kneaded with a resin to obtain a near-infrared absorbing resin composition and this resin composition is then heat-molded to produce a molded article such as a resin plate or a film;

(2) a method in which a paint or a coating solution that contains the near-infrared absorbing agent or the near-infrared absorbing composition of the present invention is prepared and then coated on a (transparent) resin plate, a (transparent) film or a (transparent) glass plate; and (3) A method of producing a laminated resin plate, a laminated resin film, a laminated glass or the like using an adhesive in which the near-infrared absorbing agent or the near-infrared absorbing composition of the present invention is incorporated.

First, in the method (1) in which the near-infrared absorbing agent or the near-infrared absorbing composition of the present invention is blended and kneaded with a resin and the resultant is heat-molded, the transparency of the resin material is preferably as high as possible when it is made into a resin plate or a resin film. Specific examples of such resin material include, but not limited to, polyethylenes; polypropylenes; polystyrenes; copolymers of polyethylene and cycloolefin such as norbornene; polyacrylic acids; polyacrylates; vinyl compounds and addition polymers thereof, such as polyvinyl acetate, polyacrylonitrile, polyvinyl chloride and polyvinyl fluoride; polymethacrylic acids; polymethacrylates; copolymers of a vinyl compound or a fluorine compound, such as polyvinylidene chloride, polyvinylidene fluoride, polyvinylidene cyanide, vinylidene fluoride/trifluoroethylene copolymers, vinylidene fluoride/tetrafluoroethylene copolymers, and vinylidene cyanide/vinyl acetate copolymers; fluorine-containing compounds such as polytrifluoroethylene, polytetrafluoroethylene and polyhexafluoropropylene; polyamides such as nylon 6 and nylon 66; polyimides; polyurethanes; polypeptides; polyesters such as polyethylene terephthalate; polyethers such as polycarbonate, polyoxymethylene, polyethylene oxide and polypropylene oxide; epoxy resins; polyvinyl alcohols; and polyvinyl butyrals.

In the production method, the processing temperature, film-forming conditions and the like are somewhat variable depending on the base resin to be used; however, normally, a near-infrared absorbing material can be obtained by a method in which the near-infrared absorbing agent or the near-infrared absorbing composition is added to powder or a pellet of the base resin and heated to 150 to 350° C. to be dissolved; the resultant is subsequently molded to prepare a resin plate or the like, or made into a film or a raw sheet using an extruder; and the thus obtained plate, film or raw sheet is stretched uniaxially or biaxially at a temperature of 30 to 120° C. and a draw ratio of 2 to 5 to obtain a 10 to 200 μm-thick film. It is noted here that, at the time of the kneading, in addition to an additive(s) normally used in ordinary resin molding such as an ultraviolet absorber, an antioxidant, a light stabilizer, a flame retardant and/or a plasticizer, a dye or a pigment for controlling the color tone or other near-infrared absorbing compound may also be added. The amount of the near-infrared absorbing compound to be added varies depending on the thickness of the resin to be produced, the desired absorption strength, the desired near-infrared transmittance, the desired solar transmittance, the desired visible light transmittance and the like; however, it is usually 1 ppm to 10%.

In the method (2) in which a paint is prepared and then coated, a method of preparing a paint by dissolving the near-infrared absorbing agent or the near-infrared absorbing composition of the present invention in a binder resin or an organic solvent, or a method of preparing an aqueous paint by dissolving or dispersing the near-infrared absorbing agent or the near-infrared absorbing composition in a binder resin and an aqueous solvent can be employed.

In the former method, usually, an aliphatic ester-based resin, an acrylic resin, a melamine resin, a urethane resin, an aromatic ester-based resin, a polycarbonate resin, an aliphatic polyolefin resin, an aromatic polyolefin resin, a polyvinyl-based resin, a polyvinyl alcohol resin, a polyvinyl-based modified resin (such as PVB or EVA) or a copolymer resin thereof is used as the binder. As the solvent, a halogen-based, alcohol-based, ketone-based, ester-based, aliphatic hydrocarbon-based, aromatic hydrocarbon-based or ether-based solvent, or a mixed system thereof is used. The concentration of the near-infrared absorbing composition varies depending on the coating thickness, the desired absorption strength, the desired near-infrared transmittance, the desired solar transmittance, the desired visible light transmittance and the like; however, it is usually 0.1 to 100% by mass with respect to the weight of the binder resin. Further, the concentration of the binder resin is usually 1 to 50% by mass with respect to the whole paint.

In the latter case, for example, a method of dissolving or dispersing the near-infrared absorbing agent or the near-infrared absorbing composition in an aqueous binder resin, or a method of making the near-infrared absorbing composition into fine particles of several micrometers or less in size and then preparing an emulsion by dispersing the fine particles in an aqueous solvent using an emulsifier as required can be employed.

Examples of the aqueous binder resin include polyvinyl alcohols and modification products thereof; polyacrylic acids and copolymers thereof; and celluloses and modification products thereof. Examples of the aqueous solvent include water; and solvents prepared by adding an alcohol such as methyl alcohol, a ketone such as acetone or an ether such as tetrahydrofuran to water.

Further, examples of the emulsion include those in which pulverized near-infrared absorbing composition (50 to 500 nm) is dispersed in an uncolored acrylic emulsion paint such as an acrylic emulsion-type aqueous paint dispersed in an acrylic emulsion.

To the paint, in addition to an additive(s) normally used in paints such as an ultraviolet absorber, an antioxidant and/or a light stabilizer, a dye or a pigment for controlling the color tone or other near-infrared absorbing compound may also be added. The paint prepared by the above-described method is coated on a transparent resin film, a transparent resin, a transparent glass or the like using a bar coater, a gravure coater, a comma coater, a rip coater, a curtain coater, a roll coater, a blade coater, a spin coater, a reverse coater or a die coater or by spraying or the like, thereby a near-infrared absorbing material is produced. It is also possible to arrange a protective layer for protecting the coated surface or to laminate a transparent resin plate, a transparent resin film or the like on the coated surface. Further, a cast film is also included in this method.

In the method (3) where a laminated resin plate, a laminated resin film, a laminated glass or the like is produced using an adhesive in which the near-infrared absorbing agent or the near-infrared absorbing composition is incorporated, as the adhesive, a known transparent adhesive for laminated glasses, for example, a polyvinyl butyral (PVB) adhesive or an ethylene-vinyl acetate (EVA) adhesive for common resins such as silicon-based, urethane-based and acrylic resins or for laminated glasses, can be used. Using an adhesive in which the near-infrared absorbing agent or the near-infrared absorbing composition is added in an amount of 0.1 to 50% by mass, resin plates, a resin plate and a resin film, a resin plate and a glass, resin films, a resin film and a glass, or glasses are adhered with each other to prepare a near-infrared absorbing material. Alternatively, a thermocompression bonding method may be employed as well.

It is particularly preferred that the near-infrared absorbing agent or the near-infrared absorbing composition of the present invention be used as a near-infrared absorbing resin composition. The synthetic resin used in the near-infrared absorbing resin composition of the present invention will now be described.

Examples of a synthetic resin that can be used in the present invention include thermoplastic resins, thermosetting resins, fluorine based resin and silicone resins.

Examples of the thermoplastic resins include a-olefin polymers such as polypropylenes, high-density polyethylenes, low-density polyethylenes, linear low-density polyethylenes, cross-linked polyethylenes, ultrahigh-molecular-weight polyethylenes, polybutene-1, poly-3-methylpentene and poly-4-methylpentene; polyolefin-based resins and copolymers thereof, such as ethylene-vinyl acetate copolymers, ethylene-ethyl acrylate copolymers, ethylene-propylene copolymers, and copolymers of a polyethylene and a cycloolefin such as norbornene; halogen-containing resins, such as polyvinyl chloride, polyvinylidene chloride, chlorinated polyethylene, chlorinated polypropylene, polyvinylidene fluoride, chlorinated rubbers, vinyl chloride-vinyl acetate copolymers, vinyl chloride-ethylene copolymers, vinyl chloride-vinylidene chloride copolymers, vinyl chloride-vinylidene chloride-vinyl acetate ternary copolymers, vinyl chloride-acrylate copolymers, vinyl chloride-maleate copolymers and vinyl chloride-cyclohexylmaleimide copolymers; petroleum resins; coumarone resins; polystyrenes; polyvinyl acetates; acrylic resins; copolymers (e.g., AS resins, ABS resins, ACS resins, SBS resins, MBS resins and heat-resistant ABS resins) that are composed of styrene and/or α-methylstyrene with other monomer (e.g., maleic anhydride, phenyl maleimide, methyl methacrylate, butadiene or acrylonitrile); polymethyl methacrylates; polyvinyl alcohols; polyvinyl formals; polyvinyl butyrals; aromatic polyesters, including polyalkylene terephthalates such as polyethylene terephthalate, polybutylene terephthalate and polycyclohexane dimethylene terephthalate, and polyalkylene naphthalates such as polyethylene naphthalate and polybutylene naphthalate, and linear polyesters such as polytetramethylene terephthalate; degradable aliphatic polyesters such as polyhydroxy butyrate, polycaprolactone, polybutylene succinate, polyethylene succinate, polylactic acid, polymalic acid, polyglycolic acid, polydioxane and poly(2-oxetanone); polyamides such as polyphenylene oxide, polycaprolactam and polyhexamethylene adipamide; polycarbonates; polycarbonate/ABS resins; branched polycarbonates; polyacetals; polyphenylene sulfides; polyurethanes; cellulose-based resins; polyimide resins; and blends of these thermoplastic resins.

Further, the thermoplastic resin may also be an elastomer, such as an isoprene rubber, a butadiene rubber, an acrylonitrile-butadiene copolymer rubber, a styrene-butadiene copolymer rubber, a fluorine rubber, a silicone rubber, an olefin-based elastomer, a styrene-based elastomer, a polyester-based elastomer, a nitrile-based elastomer, a nylon-based elastomer, a vinyl chloride-based elastomer, a polyamide-based elastomer or a polyurethane-based elastomer.

Examples of the thermosetting resins include phenol resins, urea resins, melamine resins, epoxy resins and unsaturated polyester resins.

Examples of the synthetic resin further include silicone rubber-polyethersulfones, polysulfones, polyphenylene ethers, polyether ketones, polyether ether ketones and liquid crystal polymers.

In the present invention, these synthetic resins may be used individually, or two or more thereof may be used in combination. Further, the synthetic resins may be alloyed as well.

These synthetic resins can be used regardless of the molecular weight, the polymerization degree, the density, the softening point, the ratio of insoluble component(s) in a solvent, the degree of stereoregularity, the presence or absence of a catalyst residue, the type and incorporation ratio of each material monomer, the type of the polymerization catalyst (for example, a Ziegler catalyst or a metallocene catalyst).

Among the above-described synthetic resins, the thermoplastic resins are preferred from the standpoints of the compatibility and the processability of the phthalocyanine compound represented by the Formula (1). Particularly, among the thermoplastic resins, polycarbonate and polymethyl methacrylate are preferred because of their transparency and near-infrared absorbing properties.

In the near-infrared absorbing resin composition of the present invention, the total content of the phthalocyanine compound represented by the Formula (1) is preferably 0.001 to 20 parts by mass, more preferably 0.01 to 10 parts by mass, most preferably 0.1 to 5 parts by mass, with respect to 100 parts by mass of the above-described synthetic resin.

When the total content of the phthalocyanine compound represented by the Formula (1) is less than 0.001 parts by mass, sufficient near-infrared absorbing capacity may not be achieved, whereas when the total content exceeds 20 parts by mass, not only it is uneconomical because an effect corresponding to the amount of use cannot be attained, but also the transparency in the visible light region may be impaired.

The near-infrared absorbing agent or the near-infrared absorbing composition of the present invention can be blended into the synthetic resin in accordance with a conventional method, which is not particularly restricted. For example, in cases where a thermoplastic resin is used as the synthetic resin, any method normally used for blending various additives into a thermoplastic resin can be employed, and the near-infrared absorbing agent or the near-infrared absorbing composition of the present invention may be incorporated into the thermoplastic resin by mixing and kneading them, for example, by roll kneading or bumper kneading or using an extruder or a kneader.

Alternatively, a near-infrared absorbing resin composition solution in which the near-infrared absorbing agent or the near-infrared absorbing composition and the above-described synthetic resin are dissolved or dispersed in a solvent may be formulated and used.

As required, the near-infrared absorbing resin composition of the present invention may also be stabilized by incorporating an additive(s) used in synthetic resins, such as a phenolic antioxidant, a phosphorus-based antioxidant, a thioether-based antioxidant, an ultraviolet absorber and/or a hindered amine-based light stabilizer.

Examples of the above-described phenolic antioxidant include 2,6-di-tert-butyl-p-cresol, 2,6-diphenyl-4-octadecyloxyphenol, distearyl(3,5-di-tert-butyl-4-hydroxybenzyl)phosphonate, 1,6-hexamethylene-bis[(3,5-di-tert-butyl-4-hydroxyphenyl)propionic acid amide], 4,4'-thiobis(6-tert-butyl-m-cresol), 2,2'-methylene-bis(4-methyl-6-tert-butylphenol), 2,2'-methylene-bis(4-ethyl-6-tert-butyl phenol), 4,4'-butylidene-bis(6-tert-butyl-m-cresol), 2,2'-ethylidene-bis(4,6-di-tert-butylphenol), 2,2'-ethylidene-bis(4-sec-butyl-6-tert-butylphenol), 1,1,3-tris(2-methyl-4-hydroxy-5-tert-butylphenyl)butane, 1,3,5-tris(2,6-dimethyl-3-hydroxy-4-tert-butylbenzyl)isocyanurate, 1,3,5-tris(3,5-di-tert-butyl-4-hydroxybenzyl)isocyanurate, 1,3,5-tris(3,5-di-tert-butyl-4-hydroxybenzyl)-2,4,6-trimethylbenzene, 2-tert-butyl-4-methyl-6-(2-acryloyloxy-3-tert-butyl-5-methylbenzyl)phenol, stearyl(3,5-di-tert-butyl-4-hydroxyphenyl)propionate, tetrakis[methyl-3-(3,5-di-tert-butyl-4-hydroxyphenyl)propionate]methane, thiodiethylene glycol-bis[(3,5-di-tert-butyl-4-hydroxyphenyl)propionate], 1,6-hexamethylene-bis[(3,5-di-tert-butyl-4-hydroxyphenyl)propionate], bis[3,3-bis(4-hydroxy-3-tert-butylphenyl)butyric acid]glycol ester, bis[2-tert-butyl-4-methyl-6-(2-hydroxy-3-tert-butyl-5-methylbenzyl)phenyl]terephthalate, 1,3,5-tris[(3,5-di-tert-butyl-4-hydroxyphenyl)propionyloxyethyl]isocyanurate, 3,9-bis[1,1-dimethyl-2-{(3-tert-butyl-4-hydroxy-5-methylphenyl)propionyloxy}ethyl]-2,4,8,10-tetraoxaspiro[5,5]undecane and triethylene glycol-bis[(3-tert-butyl-4-hydroxy-5-methylphenyl)propionate]. These phenolic antioxidants are used in an amount of preferably 0.001 to 10 parts by mass, more preferably 0.05 to 5 parts by mass, with respect to 100 parts by mass of the synthetic resin.

Examples of the above-described phosphorus-based antioxidant include trisnonylphenyl phosphite, tris[2-tert-butyl-4-(3-tert-butyl-4-hydroxy-5-methylphenylthio)-5-methylphenyl]phosphite, tridecyl phosphite, octyldiphenyl phosphite, di(decyl)monophenyl phosphite, di(tridecyl)pentaerythritol diphosphite, di(nonylphenyl)pentaerythritol diphosphite, bis(2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, bis(2,4-dicumylphenyl)pentaerythritol diphosphite, tetra(tridecyl)isopropylidene diphenol diphosphite, tetra(tridecyl)-4,4'-n-butylidene-bis(2-tert-butyl-5-methylphenol) diphosphite, hexa(tridecyl)-1,1,3-tris(2-methyl-4-hydroxy-5-tert-butylphenyl)butane triphosphite, tetrakis(2,4-di-tert-butylphenyl)biphenylene diphosphonite, 9,10-dihydro-9-oxa-10-phosphaphenanthrene-10-oxide, 2,2'-methylene-bis(4,6-tert-butylphenyl)-2-ethylhexyl phosphite, 2,2'-methylene-bis(4,6-tert-butylphenyl)-octadecyl phosphite, 2,2'-ethylidene-bis(4,6-di-tert-butylphenyl)fluorophosphite, tris(2-[(2,4,8,10-tetrakis-tert-butyldibenzo[d,f][1,3,2]dioxaphosphepin-6-yl)oxy]ethyl) amine, and phosphites of 2-ethyl-2-butylpropylene glycol and 2,4,6-tri-tert-butylphenol. These phosphorus-based antioxidants are used in an amount of preferably 0.001 to 10 parts by mass, more preferably 0.05 to 5 parts by mass, with respect to 100 parts by mass of the synthetic resin.

Examples of the above-described thioether-based antioxidant include dialkyl thiodipropionates such as dilauryl thiodipropionate, dimyristyl thiodipropionate and distearyl thiodipropionate; and pentaerythritol tetra(β-alkylmercapto)propionic acid esters. These phosphorus-based antioxidants are used in an amount of preferably 0.001 to 10 parts by mass, more preferably 0.05 to 5 parts by mass, with respect to 100 parts by mass of the synthetic resin.

Examples of the above-described ultraviolet absorber include 2-hydroxybenzophenones such as 2,4-dihydroxybenzophenone, 2-hydroxy-4-methoxybenzophenone, 2-hydroxy-4-octoxybenzophenone, and 5,5'-methylene-bis(2-hydroxy-4-methoxybenzophenone); 2-(2'-hydroxyphenyl)benzotriazoles such as 2-(2'-hydroxy-5'-methylphenyl)benzotriazole, 2-(2'-hydroxy-3',5'-di-tert-butylphenyl)-5-chlorobenzotriazole, 2-(2'-hydroxy-3'-tert-butyl-5'- methylphenyl)-5-chlorobenzotriazole, 2-(2'-hydroxy-5'-tert-octylphenyl)benzotriazole, 2-(2'-hydroxy-3',5'-dicumylphenyl)benzotriazole, 2,2'-methylene-bis(4-tert-octyl-6-(benzotriazolyl)phenol) and 2-(2'-hydroxy-3'-tert-butyl-5'-carboxyphenyl)benzotriazole; benzoates such as phenyl salicylate, resorcinol monobenzoate, 2,4-di-tert-butylphenyl-3,5-di-tert-butyl-4-hydroxybenzoate, 2,4-di-tert-amyl phenyl-3,5-di-tert-butyl-4-hydroxybenzoate and hexadecyl-3,5-di-tert-butyl-4-hydroxybenzoate; substituted oxanilides such as 2-ethyl-2'-ethoxyoxanilide and 2-ethoxy-4'-dodecyloxanilide; cyanoacrylates such as ethyl-α-cyano-β,β-diphenylacrylate and methyl-2-cyano-3-methyl-3-(p-methoxyphenyl)acrylate; and triaryltriazines such as 2-(2-hydroxy-4-octoxyphenyl)-4,6-bis(2,4-di-tert-butylphenyl)-s-triazine, 2-(2-hydroxy-4-methoxyphenyl)-4,6-diphenyl-s-triazine and 2-(2-hydroxy-4-propoxy-5-methylphenyl)-4,6-bis(2,4-di-tert-butylphenyl)-s-triazine. These ultraviolet absorbers are used in an amount of preferably 0.001 to 30 parts by mass, more preferably 0.05 to 10 parts by mass, with respect to 100 parts by mass of the synthetic resin.

Examples of the above-described hindered amine-based light stabilizer include hindered amine compounds such as 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl)sebacate, bis(1,2,2,6,6-tetramethyl-4-piperidyl)sebacate, bis(1-octoxy-2,2,6,6-tetramethyl-4-piperidyl)sebacate, tetrakis(2,2,6,6-tetramethyl-4-piperidyl)-1,2,3,4-butane tetracarboxylate, tetrakis(1,2,2,6,6-pentamethyl-4-piperidyl)-1,2,3,4-butane tetracarboxylate, bis(2,2,6,6-tetramethyl-4-piperidyl)-di(tridecyl)-1,2,3,4-butane tetracarboxylate, bis(1,2,2,6,6-pentamethyl-4-piperidyl)-di(tridecyl)-1,2,3,4-butane tetracarboxylate, bis(1,2,2,4,4-pentamethyl-4-piperidyl)-2-butyl-2-(3,5-di-tert-butyl-4-hydroxybenzyl)malonate, 1-(2-hydroxyethyl)-2,2,6,6-tetramethyl-4-piperidinol/diethyl succinate polycondensate, 1,6-bis(2,2,6,6-tetramethyl-4-piperidylamino)hexane/2,4-dichloro-6-morpholino-s-triazine polycondensate, 1,6-bis(2,2,6,6-tetramethyl-4-piperidylamino)hexane/2,4-dichloro-6-tert-octylamino-s-triazine polycondensate, 1,5,8,12-tetrakis[2,4-bis(N-butyl-N-(2,2,6,6-tetramethyl-4-piperidyl)amino)-s-triazine-6-yl]-1,5,8,12-tetraazadodecane, 1,5,8,12-tetrakis[2,4-bis(N-butyl-N-(1,2,2,6,6-pentamethyl-4-piperidyl)amino)-s-triazine-6-yl]-1,5,8,12-tetraazadodecane, 1,6,11-tris[2,4-bis(N-butyl-N-(2,2,6,6-tetramethyl-4-piperidyl)amino)-s-triazine-6-yl]amino undecane, and 1,6,11-tris[2,4-bis(N-butyl-N-(1,2,2,6,6-pentamethyl-4-piperidyl)amino)-s-triazine-6-yl]amino undecane. The hindered amine-based light stabilizers are used in an amount of preferably 0.001 to 30 parts by mass, more preferably 0.05 to 10 parts by mass, with respect to 100 parts by mass of the synthetic resin.

In addition, as required, an additive(s) normally incorporated in synthetic resins, for example, a nucleating agent such as aluminum p-tert-butylbenzoate, an aromatic metal phosphate or dibenzylidene sorbitol, an antistatic agent, a metallic soap, a hydrotalcite, a triazine ring-containing compound, a metal hydroxide, a phosphoric acid ester-based flame retardant, a condensed phosphoric acid ester-based flame retardant, a phosphate-based flame retardant, an inorganic phosphorus-based flame retardant, a (poly)phosphate-based flame retardant, a halogen-based flame retardant, a silicon-based flame retardant, an antimony oxide such as antimony trioxide, other inorganic-based flame retardant aid, other organic-based flame retardant aid, a filler, a pigment, a lubricant, and/or a foaming agent, may also be added to the near-infrared absorbing resin composition of the present invention.

Examples of the above-described triazine ring-containing compound include melamine, ammeline, benzoguanamine, acetoguanamine, phthalodiguanamine, melamine cyanurate, melamine pyrophosphate, butylene diguanamine, norbornene diguanamine, methylene diguanamine, ethylene dimelamine, trimethylene dimelamine, tetramethylene dimelamine, hexamethylene dimelamine and 1,3-hexylene dimelamine.

Examples of the above-described metal hydroxide include magnesium hydroxide, aluminum hydroxide, calcium hydroxide, barium hydroxide, zinc hydroxide and KISUMA 5A (magnesium hydroxide: manufactured by Kyowa Chemical Industry Co., Ltd.).

Examples of the above-described phosphoric acid ester-based flame retardant include trimethyl phosphate, triethyl phosphate, tributyl phosphate, tributoxyethyl phosphate, trischloroethyl phosphate, trisdichloropropyl phosphate, triphenyl phosphate, tricresyl phosphate, cresyldiphenyl phosphate, trixylenyl phosphate, octyl diphenyl phosphate, xylenyl diphenyl phosphate, trisisopropylphenyl phosphate, 2-ethylhexyl diphenyl phosphate, t-butylphenyl diphenyl phosphate, bis-(t-butylphenyl)phenyl phosphate, tris-(t-butylphenyl)phosphate, isopropylphenyl diphenyl phosphate, bis-(isopropylphenyl)diphenyl phosphate and tris-(isopropylphenyl)phosphate.

Examples of the above-described condensed phosphoric acid ester-based flame retardant include 1,3-phenylene-bis (diphenylphosphate), 1,3-phenylene-bis(dixylenylphosphate) and bis-phenol A-bis(diphenylphosphate).

Examples of the above-described (poly)phosphate-based flame retardant include ammonium salts and amine salts of polyphosphoric acids, such as ammonium polyphosphate, melamine polyphosphate, piperazine polyphosphate, melamine pyrophosphate and piperazine pyrophosphate.

Examples of the above-described other inorganic flame retardant aid include inorganic compounds such as titanium oxide, aluminum oxide, magnesium oxide, hydrotalcites, talc and montmorillonite, and surface-treated products thereof. For example, a variety of commercially available products such as TIPAQUE R-680 (titanium oxide: manufactured by Ishihara Sangyo Kaisha, Ltd.), KYOWAMAG 150 (magnesium oxide: manufactured by Kyowa Chemical Industry Co., Ltd.), DHT-4A (hydrotalcite: manufactured by Kyowa Chemical Industry Co., Ltd.) and ALCAMIZER 4 (zinc-modified hydrotalcite: manufactured by Kyowa Chemical Industry Co., Ltd.) can be used.

Examples of the above-described other organic flame retardant aid include pentaerythritol.

In addition, in the near-infrared absorbing resin composition of the present invention, as required, an additive(s) normally used in synthetic resins, for example, a cross-linking agent, an anti-fogging agent, an anti-plate-out agent, a surface treatment agent, a plasticizer, a lubricant, a fluorescent agent, an antifungal agent, an antibacterial agent, a foaming agent, a metal inactivator, a mold-release agent, a pigment and/or a processing aid, may also be incorporated in such a range that does not impair the effects of the present invention.

In cases where an arbitrary additive(s) is/are incorporated into the near-infrared absorbing resin composition of the present invention in addition to the near-infrared absorbing composition of the present invention and the above-described synthetic resin, the amount thereof can be selected as appropriate in accordance with the type(s) and the like of the additive(s); however, from the standpoint of not impairing the effects of the present invention, the total amount of the additive(s) is preferably 20 parts by mass or less with respect to 100 parts by mass of the synthetic resin.

By molding the near-infrared absorbing resin composition of the present invention, a molded article can be obtained as a near-infrared absorbing material. The molding method is not particularly restricted, and examples thereof include extrusion processing, calender processing, injection molding, rolling, compression molding and blow molding. Molded articles having various shapes, such as resin plates, sheets, films, fibers and special shape articles, can be thereby produced.

Further, by dissolving the near-infrared absorbing resin composition of the present invention in various solvents and preparing cast films therefrom, near-infrared absorbing films can be obtained as near-infrared absorbing materials.

Such near-infrared absorbing materials obtained from the near-infrared absorbing resin composition of the present invention have excellent near-infrared absorbing capacity.

The near-infrared absorbing resin composition and the near-infrared absorbing material of the present invention can be used in a variety of applications where near-infrared absorbing capacity (heat ray-absorbing capacity) is required, for example, optical information recording materials such as optical cards, organic photoconductors, laser heat transfer recording materials, laser heat-sensitive recording materials and materials for laser direct plate making; various optical filters for near-infrared absorption, such as filters for plasma displays, optical filters for thin displays and optical filters for photosemiconductor devices; heat ray-shielding materials, heat ray-shielding films and heat ray-shielding resin glasses; thermal insulation/storage fibers; protective spectacles; agricultural films; automobile interior and exterior materials; sheets; other various resin molded articles; secret inks; coating materials; and solar cell members.

EXAMPLES

The present invention will now be described more concretely by way of examples and the like thereof. It is noted here that, in the following examples and the like, "%" and "ppm" are based on mass unless otherwise specified.

Synthesis Example 1

<Synthesis of Phthalocyanine Compound in which Ratio of Cyclic Structure of Formula (2) and Cyclic Structure of Formula (4) is 1:1>

In a 10-ml eggplant-type flask, 0.5 g of 1,4-dibutoxy-2,3-dicyanoanthracene, 0.44 g of 1,4-dibutoxy-2,3-dicyanonaphthalene, 0.15 g of sodium methoxide and 1.8 ml of n-butanol were added and allowed to react for 6 hours under a nitrogen atmosphere at 135° C. After cooling the resultant, methanol was added thereto and the resulting precipitate was filtered and purified with chloroform, thereby obtaining a composition of a phthalocyanine compound in an amount of 0.45 g (yield: 50%).

By measuring the NMR of the thus obtained composition, it was confirmed that the composition contained the cyclic structure of the Formula (2) and the cyclic structure of the Formula (4) at a ratio of 1:1 (the NMR chart is shown in FIG. 1).

In addition, the absorption spectrum of a chloroform solution of the thus obtained composition was measured. The measurement was performed using V-670 manufactured by JASCO Corporation. The thus obtained absorption spectrum is shown in FIG. 4. The maximum absorption wavelength, λmax, was 912 nm, and the molar extinction coefficient, ε, was $1.8 \times 10^5$ $cm^{-1}mol^{-1}$.

Synthesis Example 2

<Synthesis of Compound in which Ratio of Cyclic Structure of Formula (2) and Cyclic Structure of Formula (4) is 1:3>

In a 10-ml eggplant-type flask, 0.5 g of 1,4-dibutoxy-2,3-dicyanoanthracene, 0.145 g of 1,4-dibutoxy-2,3-dicyanonaphthalene, 0.1 g of sodium methoxide and 1.4 ml of n-butanol were added and allowed to react for 6 hours under a nitrogen atmosphere at 135° C. After cooling the resultant, methanol was added thereto and the resulting precipitate was filtered and purified with chloroform, thereby obtaining a composition of a phthalocyanine compound in an amount of 0.33 g (yield: 51%).

By measuring the NMR of the thus obtained composition, it was confirmed that the composition contained the cyclic structure of the Formula (2) and the cyclic structure of the Formula (4) at a ratio of 1:3 (the NMR chart is shown in FIG. 2).

In addition, the absorption spectrum of a chloroform solution of the thus obtained composition was measured. The measurement was performed using V-670 manufactured by JASCO Corporation. The thus obtained absorption spectrum is shown in FIG. 4. The maximum absorption wavelength, λmax, was 943 nm, and the molar extinction coefficient, ε, was $1.8 \times 10^5$ $cm^{-1}mol^{-1}$.

Synthesis Example 3

<Synthesis of Compound in which Ratio of Cyclic Structure of Formula (2) and Cyclic Structure of Formula (4) is 1:6>

In a 10-ml eggplant-type flask, 0.7 g of 1,4-dibutoxy-2,3-dicyanoanthracene, 0.1 g of 1,4-dibutoxy-2,3-dicyanonaphthalene, 0.12 g of sodium methoxide and 1.4 ml of n-butanol were added and allowed to react for 6 hours under a nitrogen atmosphere at 135° C. After cooling the resultant, methanol was added thereto and the resulting precipitate was filtered and purified with chloroform, thereby obtaining a composition of a phthalocyanine compound in an amount of 0.24 g (yield: 31%). By measuring the NMR of the thus obtained composition, it was confirmed that the composition contained the cyclic structure of the Formula (2) and the cyclic structure of the Formula (4) at a ratio of 1:6 (the NMR chart is shown in FIG. 3).

In addition, the absorption spectrum of a chloroform solution of the thus obtained composition was measured. The measurement was performed using V-670 manufactured by JASCO Corporation. The thus obtained absorption spectrum is shown in FIG. 4. The maximum absorption wavelength, λmax, was 950 nm, and the molar extinction coefficient, ε, was $2.0 \times 10^5$ $cm^{-1}mol^{-1}$.

Synthesis Example 4

<Introduction of Copper into Compound in which Ratio of Cyclic Structure of Formula (2) and Cyclic Structure of Formula (4) is 1:6>

In a 10-ml eggplant-type flask, 0.3 g of the mixture of the phthalocyanine compound obtained in Synthesis Example 3, 0.07 g of copper (II) acetyl acetonate and 3 ml of chlorobenzene were added and stirred for 4 hours under a nitrogen atmosphere at 150° C. After cooling the resultant, methanol was added thereto and the resulting precipitate was recovered by filtration to obtain a composition of a copper phthalocyanine compound in an amount of 0.3 g (yield: 96%).

The absorption spectrum of a chloroform solution of the thus obtained composition was measured. The measurement was performed using V-670 manufactured by JASCO Corporation. The thus obtained absorption spectrum is shown in FIG. 5. The maximum absorption wavelength, λmax, was 893 nm, and the molar extinction coefficient, ε, was $1.8 \times 10^5$ $cm^{-1}mol^{-1}$.

Synthesis Example 5

<Introduction of Nickel into Compound in which Ratio of Cyclic Structure of Formula (2) and Cyclic Structure of Formula (4) is 1:6 (Naphthalene:Anthracene=1:6)>

In a 10-ml eggplant-type flask, 0.3 g of the mixture of the phthalocyanine compound obtained in Synthesis Example 3, 0.07 g of nickel acetyl acetonate and 3 ml of chlorobenzene were added and stirred for 4 hours under a nitrogen atmosphere at 150° C. After cooling the resultant, methanol was added thereto and the resulting precipitate was recovered by filtration to obtain a composition of a nickel phthalocyanine compound in an amount of 0.3 g (yield: 96%).

The absorption spectrum of a chloroform solution of the thus obtained composition was measured. The measurement was performed using V-670 manufactured by JASCO Corporation. The thus obtained absorption spectrum is shown in FIG. 5. The maximum absorption wavelength, λmax, was 899 nm, and the molar extinction coefficient, ε, was $1.8 \times 10^5$ $cm^{-1}mol^{-1}$.

Synthesis Example 6

<Synthesis of Phthalocyanine Compound in which Ratio of Cyclic Structure of Formula (3) and Cyclic Structure of Formula (4) is 1:1>

In a 10-ml eggplant-type flask, 0.3 g of 1,4-dibutoxy-2,3-dicyanoanthracene, 0.26 g of 1,4-dibutoxy-2,3-dicyano-5-quinoline, 0.09 g of sodium methoxide and 1.4 ml of n-butanol were added and allowed to react for 6 hours under a nitrogen atmosphere at 135° C. After cooling the resultant, methanol was added thereto and the resulting precipitate was filtered to obtain a composition of a phthalocyanine compound in an amount of 0.25 g (yield: 41%).

By measuring the NMR of the thus obtained composition, it was confirmed that the composition contained the cyclic structure of the Formula (3) and the cyclic structure of the Formula (4) at a ratio of 1:1.

Comparative Synthesis Example 1

<Synthesis of Octabutoxynaphthalocyanine H2>

In a 10-ml eggplant-type flask, 1 g of 1,4-dibutoxy-2,3-dicyanonaphthalene, 0.17 g of sodium methoxide and 1.5 ml of n-butanol were added and allowed to react for 6 hours under a nitrogen atmosphere at 135° C. After cooling the resultant, methanol was added thereto and the resulting precipitate was filtered and purified with chloroform, thereby obtaining the desired compound in an amount of 0.3 g (yield: 30%). In addition, the absorption spectrum of a chloroform solution of the thus obtained composition was measured. The measurement was performed using V-670 manufactured by JASCO Corporation. The thus obtained absorption spectrum is shown in FIG. 4. The maximum absorption wavelength, ?max, was 869 nm.

Comparative Synthesis Example 2

<Synthesis of Octabutoxyanthracene Azaporphyrin H2>

In a 10-ml eggplant-type flask, 1 g of 1,4-dibutoxy-2,3-dicyanoanthracene, 0.15 g of sodium methoxide and 1.5 ml of n-butanol were added and allowed to react for 6 hours under a nitrogen atmosphere at 135° C. After cooling the resultant, methanol was added thereto and the resulting precipitate was filtered and purified with chloroform to obtain yellow powder. It was confirmed that this powder does not absorb near-infrared radiation and that octabutoxyanthracene azaporphyrin H2 was not synthesized.

Example 1

<Production of Near-Infrared Absorbing Resin Composition and Near-Infrared Absorbing Material>

A near-infrared absorbing resin composition was obtained by blending the mixture of the phthalocyanine compound obtained in the above-described Synthesis Example 3 in an amount of 0.004 parts by mass with respect to 100 parts by mass of a cycloolefin copolymer, TOPAS (registered trademark) (a copolymer of norbornene and ethylene; manufactured by Polyplastics Co., Ltd.). The thus obtained composition was melt-kneaded at 230° C. and subsequently injection-molded to obtain a 10×10×2 mm near-infrared absorbing material.

The absorption spectrum of the thus obtained near-infrared absorbing material was measured. The measurement was performed against an air blank using V-670 manufactured by JASCO Corporation. The thus obtained absorption spectrum is shown in FIG. 6. The maximum absorption wavelength, λmax, was 955 nm and the transmittance at this wavelength was 16%.

Further, the transmittance of visible light (380 nm to 750 nm) was determined in accordance with JIS R3106 and the haze value was measured. The results thereof are shown in Table 1.

Comparative Example 1

The measurements were performed in the same manner as in Example 1, except that the phthalocyanine compound was not blended.

TABLE 1

|  | Example 1 | Comparative Example 1 |
|---|---|---|
| Test compound | Synthesis Example 3 | none |
| Maximum absorption wavelength of compound | 949 | — |
| Transparency (%) of test piece at maximum absorption wavelength (955 nm) | 16 | 92 |
| Transparency of visible light (380 to 750 nm) | 77 | 90 |
| Haze value (%) | 1.4 | 1.4 |

The invention claimed is:

1. A near-infrared absorbing agent, comprising a phthalocyanine compound represented by the following Formula (1):

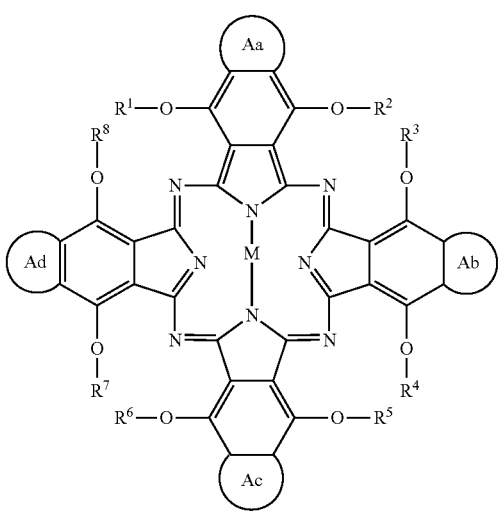

(1)

wherein M represents two hydrogen atoms, a divalent metal atom, a trivalent substituted metal atom, a tetravalent substituted metal atom, or an oxymetal atom; $R^1$ to $R^8$ may be the same or different from each other and each represent an alkyl group having 1 to 20 carbon atoms which is optionally substituted, an aryl group having 6 to 20 carbon atoms which is optionally substituted, an arylalkyl group having 7 to 20 carbon atoms which is optionally substituted, or a cycloalkyl group having 5 to 12 carbon atoms which is optionally substituted; and Aa, Ab, Ac and Ad each independently represent a cyclic structure represented by the following Formula (2), (3) or (4), with a proviso that at least one, but not all, of said Aa, Ab, Ac and Ad is said cyclic structure represented by said Formula (4) and at least one of said Aa, Ab, Ac, and Ad is represented by Formula (3);

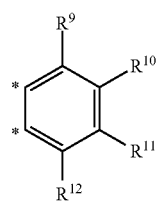

(2)

wherein $R^9$ to $R^{12}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and said Formula (2) is bound to said Formula (1) at * positions;

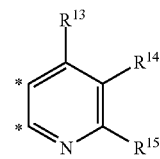

(3)

wherein $R^{13}$ to $R^{15}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and said Formula (3) is bound to said Formula (1) at * positions;

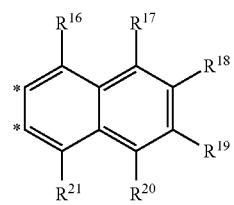

(4)

wherein $R^{16}$ to $R^{21}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and said Formula (4) is bound to said Formula (1) at * positions.

2. A near-infrared absorbing composition, comprising at least one near-infrared absorbing agent according to claim 1.

3. A near-infrared absorbing material, comprising at least one near-infrared absorbing agent according to claim 1.

4. A near-infrared absorbing resin composition, comprising:

a near-infrared absorbing agent; and a synthetic resin;

wherein the near-infrared absorbing agent comprises a phthalocyanine compound represented by the following Formula (1):

(1)

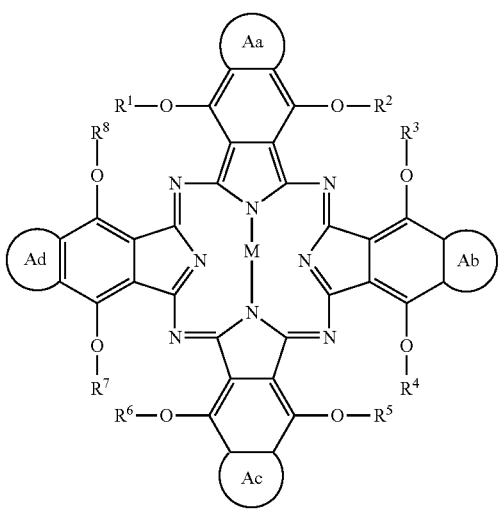

wherein M represents two hydrogen atoms, a divalent metal atom, a trivalent substituted metal atom, a tetravalent substituted metal atom, or an oxymetal atom; $R^1$ to $R^8$ may be the same or different from each other and each represent an alkyl group having 1 to 20 carbon atoms which is optionally substituted, an aryl group having 6 to 20 carbon atoms which is optionally substituted, an arylalkyl group having 7 to 20 carbon atoms which is optionally substituted, or a cycloalkyl group having 5 to 12 carbon atoms which is optionally substituted; and Aa, Ab, Ac and Ad each independently represent a cyclic structure represented by the following Formula (2), (3) or (4), with a proviso that at least one, but not all, of said Aa, Ab, Ac and Ad is said cyclic structure represented by said Formula (4) and at least one of said Aa, Ab, Ac, and Ad is represented by Formula (3);

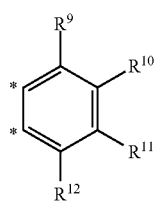

(2)

wherein $R^9$ to $R^{12}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and said Formula (2) is bound to said Formula (1) at * positions;

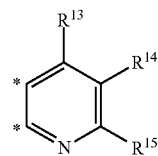

(3)

wherein $R^{13}$ to $R^{15}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and said Formula (3) is bound to said Formula (1) at * positions;

(4)

wherein, $R^{16}$ to $R^{21}$ may be the same or different from each other and each represent a hydrogen atom, a halogen atom, an alkyl group having 1 to 20 carbon atoms which is optionally substituted, an aryl group having 6 to 20 carbon atoms which is optionally substituted, an alkoxy group having 1 to 20 carbon atoms which is optionally substituted, an aryloxy group having 6 to 20 carbon atoms which is optionally substituted, an arylalkyl group having 7 to 20 carbon atoms which is optionally substituted, or a cycloalkyl group having 5 to 12 carbon atoms which is optionally substituted; and said Formula (4) is bound to said Formula (1) at * positions.

5. The near-infrared absorbing resin composition according to claim 4, wherein the total content of said phthalocyanine compound represented by said Formula (1) is 0.0005 to 20 parts by mass with respect to 100 parts by mass of said synthetic resin.

6. The near-infrared absorbing resin composition according to claim 4, wherein said synthetic resin is a thermoplastic resin.

7. A near-infrared absorbing material, obtained by molding the near-infrared absorbing resin composition according to claim 3.

8. A near-infrared absorbing material, obtained by molding the near-infrared absorbing resin composition according to claim 4.

9. A near-infrared absorbing material, obtained by molding the near-infrared absorbing resin composition according to claim 5.

10. The near-infrared absorbing resin composition according to claim 4, wherein at least one of $R^9$ to $R^{12}$ and at least one of $R^{16}$ to $R^{21}$ are not hydrogen atoms.

* * * * *